United States Patent
Milbocker et al.

(10) Patent No.: US 12,083,146 B2
(45) Date of Patent: Sep. 10, 2024

(54) MEDICAL DEVICE COMPRISING BOSWELLIC ACID

(71) Applicant: BVW Holding AG, Cham (CH)

(72) Inventors: Michael Milbocker, Holliston, MA (US); Lukas Bluecher, Eurasberg (DE)

(73) Assignee: BVW Holding AG, Cham (CH)

( * ) Notice: Subject to any disclaimer, the term of this patent is extended or adjusted under 35 U.S.C. 154(b) by 251 days.

(21) Appl. No.: 17/402,172

(22) Filed: Aug. 13, 2021

(65) Prior Publication Data

US 2022/0031734 A1 Feb. 3, 2022

Related U.S. Application Data

(63) Continuation of application No. 14/128,999, filed as application No. PCT/US2012/043462 on Jun. 21, 2012, now Pat. No. 11,123,364.

(60) Provisional application No. 61/522,169, filed on Aug. 10, 2011, provisional application No. 61/499,642, filed on Jun. 21, 2011.

(51) Int. Cl.
| | |
|---|---|
| A61K 31/19 | (2006.01) |
| A61K 31/785 | (2006.01) |
| A61K 36/324 | (2006.01) |
| A61L 29/16 | (2006.01) |
| A61L 31/04 | (2006.01) |
| A61L 31/16 | (2006.01) |
| C08G 18/34 | (2006.01) |
| C08G 18/77 | (2006.01) |

(52) U.S. Cl.
CPC ............ *A61K 31/785* (2013.01); *A61K 31/19* (2013.01); *A61K 36/324* (2013.01); *A61L 29/16* (2013.01); *A61L 31/041* (2013.01); *A61L 31/16* (2013.01); *C08G 18/348* (2013.01); *C08G 18/771* (2013.01); *A61L 2300/30* (2013.01)

(58) Field of Classification Search
None
See application file for complete search history.

(56) References Cited

U.S. PATENT DOCUMENTS

| | | |
|---|---|---|
| 4,383,050 A | 5/1983 | Nissen et al. |
| 5,064,823 A | 11/1991 | Lee et al. |
| 5,268,178 A | 12/1993 | Calhoun et al. |
| 5,411,737 A | 5/1995 | Hsu et al. |
| 5,571,080 A | 11/1996 | Jensen |
| 5,624,909 A | 4/1997 | Rao et al. |
| 5,629,351 A | 5/1997 | Taneja et al. |
| 5,676,967 A | 10/1997 | Williams et al. |
| 5,679,644 A | 10/1997 | Narasinga et al. |
| 5,691,386 A | 11/1997 | Inman et al. |
| 5,720,975 A | 2/1998 | Etzel |
| 5,837,690 A | 11/1998 | Rao et al. |
| 5,869,079 A | 2/1999 | Wong et al. |
| 5,882,660 A | 3/1999 | Chambers et al. |
| 5,888,514 A | 3/1999 | Weisman |
| 5,919,821 A | 7/1999 | Simmet et al. |
| 5,947,893 A | 9/1999 | Agrawal et al. |
| 6,022,554 A | 2/2000 | Lee et al. |
| 6,080,725 A | 6/2000 | Marciani |
| 6,174,876 B1 | 1/2001 | Simmet et al. |
| 6,207,711 B1 | 3/2001 | Matsumoto et al. |
| 6,323,183 B1 | 11/2001 | Flore |
| 6,492,429 B1 | 12/2002 | Graus et al. |
| 6,534,086 B1 | 3/2003 | Krumhar |
| 6,589,516 B1 | 7/2003 | Eyre et al. |
| 6,703,047 B2 | 3/2004 | Sawhney et al. |
| 6,777,004 B1 | 8/2004 | Wahidullah et al. |
| 6,872,225 B1 | 3/2005 | Rowan et al. |
| 6,949,260 B2 | 9/2005 | Krumhar |
| 6,949,429 B2 | 9/2005 | Kim et al. |
| 6,974,801 B2 | 12/2005 | Honda et al. |
| 7,112,573 B2 | 9/2006 | Rosazza et al. |
| 7,153,520 B2 | 12/2006 | Seo et al. |
| 7,195,790 B2 | 3/2007 | Zhang et al. |
| 7,438,925 B2 | 10/2008 | Hsu |
| 7,582,314 B2 | 9/2009 | Majeed et al. |
| 7,645,461 B2 | 1/2010 | Striggow et al. |
| 7,651,681 B1 | 1/2010 | Rose et al. |

(Continued)

FOREIGN PATENT DOCUMENTS

| | | |
|---|---|---|
| CN | 1173134 | 2/1998 |
| DE | 102008017496 | 10/2009 |

(Continued)

OTHER PUBLICATIONS

European Search Report for Application No. 12801945.2 issued on Feb. 27, 2015.

(Continued)

*Primary Examiner* — David J Blanchard
*Assistant Examiner* — Daniel F Coughlin
(74) *Attorney, Agent, or Firm* — Patterson Intellectual Property Law, P.C.; Ryan D. Levy; Mark A. Kilgore

(57) ABSTRACT

A medical composition and devices made from the composition for the delivery of extracts obtained from *Boswellia* genus, similar compounds synthetically derived, and in particular derivatives of triterpenes is disclosed. The medical device may be implantable, or alternatively a device which contacts the interior of a mammalian body. The medical device may be comprised, of or present an absorbable component containing *Boswellia* derivatives, or an eluting component. When administered into a particular body site, the *Boswellia* component may be released substantially and immediately, released slowly, or not released, into the body and residing actively on the medical device surface.

13 Claims, 3 Drawing Sheets

(56) References Cited

U.S. PATENT DOCUMENTS

| | | |
|---|---|---|
| 7,741,273 B2 | 6/2010 | McKay |
| 7,749,539 B2 | 7/2010 | Domb |
| 7,754,272 B2 | 7/2010 | Rowan et al. |
| 7,811,997 B2 | 10/2010 | Zhang et al. |
| 7,842,303 B2 | 11/2010 | Kuo et al. |
| 7,919,112 B2 | 4/2011 | Pathak et al. |
| 8,168,222 B2 | 5/2012 | Kabanov et al. |
| 2002/0010168 A1 | 1/2002 | Ammon et al. |
| 2003/0195182 A1 | 10/2003 | Sasaki et al. |
| 2003/0195367 A1 | 10/2003 | Barrault et al. |
| 2003/0199581 A1 | 10/2003 | Seligson et al. |
| 2004/0073060 A1 | 4/2004 | Gokaraju et al. |
| 2004/0151792 A1 | 8/2004 | Tripp et al. |
| 2004/0166182 A1 | 8/2004 | Zhang et al. |
| 2005/0192551 A1 | 9/2005 | Reddy |
| 2005/0209169 A1 | 9/2005 | Ammon et al. |
| 2006/0073222 A1 | 4/2006 | Arntzen et al. |
| 2006/0234990 A1 | 10/2006 | Majeed et al. |
| 2006/0251702 A1 | 11/2006 | Abram et al. |
| 2006/0280811 A1 | 12/2006 | Bombardelli |
| 2007/0129317 A1 | 6/2007 | Ammon et al. |
| 2007/0155709 A1 | 7/2007 | Muhammed et al. |
| 2007/0155906 A1 | 7/2007 | Hissink et al. |
| 2007/0224143 A1 | 9/2007 | Konis et al. |
| 2007/0231345 A1 | 10/2007 | Majeed et al. |
| 2007/0231418 A1 | 10/2007 | Scheffler |
| 2007/0249711 A1 | 10/2007 | Choi et al. |
| 2007/0253943 A1 | 11/2007 | Altunkaya |
| 2007/0281047 A1 | 12/2007 | Henry et al. |
| 2007/0299285 A1 | 12/2007 | Scheffler |
| 2008/0003639 A1 | 1/2008 | Hiroaki et al. |
| 2008/0118550 A1 | 5/2008 | Martakos et al. |
| 2008/0317885 A1 | 12/2008 | Baker |
| 2008/0317886 A1 | 12/2008 | Sparkman |
| 2009/0042832 A1 | 2/2009 | Gokaraju et al. |
| 2009/0099600 A1 | 4/2009 | Moore et al. |
| 2009/0136566 A1 | 5/2009 | Krasutsky et al. |
| 2009/0169651 A1 | 7/2009 | Majeed |
| 2009/0186837 A1 | 7/2009 | Einbond et al. |
| 2009/0263460 A1 | 10/2009 | McDonald |
| 2009/0264377 A1 | 10/2009 | Einbond et al. |
| 2009/0281558 A1 | 11/2009 | Jianmin |
| 2009/0292013 A1 | 11/2009 | Sautter et al. |
| 2009/0298938 A1 | 12/2009 | Qazi et al. |
| 2010/0034758 A1 | 2/2010 | Muhammed et al. |
| 2010/0098676 A1 | 4/2010 | Gokaraju et al. |
| 2010/0098786 A1 | 4/2010 | Puri |
| 2010/0099763 A1 | 4/2010 | Choi et al. |
| 2010/0166670 A1 | 7/2010 | Ammon et al. |
| 2010/0189824 A1 | 7/2010 | Arntzen et al. |
| 2010/0190968 A1 | 7/2010 | Kim et al. |
| 2010/0209388 A1 | 8/2010 | Mazzio et al. |
| 2010/0267983 A1 | 10/2010 | Zeng et al. |
| 2010/0316739 A1 | 12/2010 | Nisis |
| 2011/0015196 A1 | 1/2011 | Parthasaradhi et al. |
| 2011/0054025 A1 | 3/2011 | Nieto et al. |
| 2011/0077227 A1 | 3/2011 | Moinet et al. |
| 2011/0077228 A1 | 3/2011 | Moinet et al. |
| 2011/0135703 A1 | 6/2011 | Shipp |
| 2012/0156259 A1 | 6/2012 | Rau et al. |

FOREIGN PATENT DOCUMENTS

| | | |
|---|---|---|
| JP | 2009102418 | 2/2009 |
| WO | 19932024154 | 5/2001 |
| WO | 2003077860 | 9/2003 |
| WO | 2005028539 | 3/2005 |
| WO | 2006017204 | 2/2006 |
| WO | 2008112289 | 9/2008 |
| WO | 2010071864 | 6/2010 |
| WO | 2010075298 | 7/2010 |
| WO | 2013112381 | 8/2013 |

OTHER PUBLICATIONS

Raja et al. "Antistaphylococcal and biofilm inhibitory activities of acetyl-11-keto-b-boswellic acid from Boswellia serrata," BMC Microbiology, Mar. 16, 2011, 11-54.

Batrakova, E., et al., "Pluronic block copolymers: Evolution of drug delivery concept from inert nanocarriers to biological responses modifiers," Journal of Controlled Release 130 (2008) 98-106.

MEDICAL DEVICE COMPRISING BOSWELLIC ACID

CROSS-REFERENCE TO RELATED APPLICATIONS

This application claims the benefit of U.S. Provisional Application No. 61/522,169 (Att. Docket MB8562PR2), filed on Aug. 10, 2011 and entitled MEDICAL DEVICE COMPRISING BOSWELLIC ACID, and U.S. Provisional Application No. 61/499,642 (Att. Docket MB8562PR), filed on Jun. 21, 2011 and entitled MEDICAL DEVICE COMPRISING BOSWELLIC ACID, and is related to U.S. Provisional Application No. 61/496,435 (Att. Docket MB8560PR), filed on Jun. 13, 2011 and entitled POLYOL MODIFIED NATURAL BOSWELLIC ACID COMPLEXES, the entire contents of all which are hereby incorporated by reference.

BACKGROUND OF THE INVENTION

1. Field of the Invention

The present invention relates to pharmacologically novel compositions derived from plants, particularly boswellic acid complex and uses thereof. Specifically, this invention relates to polyol modified natural boswellic acid complexes where the biological functionality and tissue penetration of the components has been enhanced. More generally, this invention relates to polyol modification of any biologically useful plant extract containing fine or more available hydroxyl groups.

The present invention is also an implantable or indwelling medical device comprised of biodegradable materials for controlled release of synthetic triterpenes or botanically derived extracts of *Boswellia* genus. Biodegradable matrices for triterpene delivery are useful because they obviate the need to remove non-degradable triterpene depleted devices. The ideal polymeric formulation for delivering triterpene in a controlled matter would comprise matching the hydrophobicity/hydrophilicity characteristics of a biodegradable polymer carrier to the triterpene or modified triterpene. Said polymer carrier preferably encapsulates, or contains mixed within, the incorporated triterpene. The resulting implant device should be stable under common storage conditions, have a predictable controlled degradation profile, have versatile degradation and triterpene release profiles for both hydrophilic or hydrophobic agents, be safely eliminated from the implantation site and the body shortly after the triterpene has been depleted from the carrier, be made from biocompatible components that degrade and eliminate from the body without causing acute or chronic toxicity, and be easy to make at low cost.

The present invention relates to a medical device for the sustained delivery of a triterpene or hydrophilically modified triterpene and to a process for preparing the same. More specifically, the present invention relates to an implant for preventing adhesion, repairing a wound site, or for strengthening soft tissue with sustained delivery of a triterpene comprising: i) is a carrier of polylactic acid, polylactic acid polyurethane copolymer or absorbable polyurethane; and ii) a therapeutic of triterpene or hydrophilically modified triterpene. The carrier absorbs, contains polymeric micelles for encapsulating, or traps below a layer the therapeutic.

2. Description of Related Art

Phytochemicals, in particular terpenes, extracted from *Boswellia* genus and other pharmacologically useful plants have been reported to be active in the treatment of numerous afflictions and maladies. The biological activity of *Boswellia* genus in particular has been shown to inhibit 5-lipoxygenase and leukocyte elastase. Since 5-lipoxygenase is a key enzyme in leukotriene synthesis and the leukotrienes are active agents in the inflammatory process, triterpene acids serve as anon-steroidal anti-inflammatory agents.

Numerous studies regarding modification of triterpene and triterpene delivery systems have been conducted with a variety of triterpenes and methods in art effort to maximize the efficacy and effects of triterpenes and minimize the side effects of triterpenes by efficient administration means and controlling the rate of triterpene release.

Biocompatible, biodegradable polymers have been widely used in the medical field as surgical sutures, tissue regenerative induction membranes, protective membranes for the treatment of wounds, and drug delivery systems. Among biodegradable polymers, polylactide, polyglycolide and a copolymer of lactide and glycolide, are all commercially available. They have good biocompatibility and are decomposable in the body to harmless materials such as carbon dioxide, and water.

Triterpenes are administered orally or topically and must be delivered at high concentration in order to provide for the desired pharmacological effects. In particular, triterpenes with short half-lives must be administered frequently to achieve effective plasma concentrations.

Many important *Boswellia* extracts are hydrophobic and have limited solubility in water. In order to attain the expected therapeutic effect from such extracts it is usually required that a hydrophilic form of the extract be administered to a patient. Many *Boswellia* extracts must be administered in high doses due to their low biological efficacy. The efficacy of these extracts can be enhanced by arraying several therapeutic molecules on a multi-armed polymer scaffold. Therefore, matching the hydrophilicity of a triterpeneto its intended tissue site is a key consideration in the preparation of a formulation for oral or topical use.

The following are issued patents and applications related to the present invention.

U.S. Pat. No. 5,064,823 describes pentacyclic triterpenoid compounds such as .alpha, boswellic acid and its acetate, .beta.-boswellic acid and its acetate, which have an inhibitory effect on topoisomerase I and topoisomerase II.

U.S. Pat. No. 5,624,909 describes triterpenoid acid derivatives that are similar to natural ligands to the extent that these derivatives bind to natural selectin receptors including endothelial leukocyte adhesion molecule-1 (ELAM-1) and leukocyte/endothelial cell adhesion molecule-1 (LECAM-1). U.S. Pat. No. 5,629,351 describes a mixture of boswellic acids that is anti-inflammatory and anti-ulcerogenic activities.

U.S. Pat. Nos. 5,679,644 and 5,837,690 describe triterpenoid acid derivatives that exhibit dual pharmacophobic activities, specifically selectin ligand and leukotriene biosynthetic inhibitory activities.

U.S. Pat. No. 5,691,386 describes a hypoglycemically active triterpenoid compound isolated in purified form from genus *Salacia*, processes for obtaining the novel triterpenoid compound, compositions comprising the triterpenoid compound and methods for use a hypoglycemic agent in the treatment of diabetes. The triterpenoid compound of U.S. Pat. No. 5,691,386 is obtained from *Salacia prinoides*.

U.S. Pat. No. 5,720,975 describes the use of olibanum (extract of *Boswellia*) for the prevention or treatment of Alzheimer's disease.

U.S. Pat. No. 5,882,660 describes a composition in the form of an aqueous liquid comprising a first component a) lipid composition of two components, where one component is a molecule having one long hydrocarbon chain and a hydrophilic head group and a second component is a material which comprises at least one of a compound selected from 3.beta.-sterol; squalane; squalane; saponins or sapogenins of a plant steroid or triterpenoid and a second component b) a surface active agent selected from anionic, nonionic, cationic, zwiiterionic, amphoteric surface active agents and a third component c) a deposition aid.

U.S. Pat. No. 5,888,514 describes a composition for treating joint inflammation comprised of cartilage and *Boswellia* extract.

U.S. Pat. Nos. 5,919,821 and 6,174,876 describe a vegetable preparation containing boswellic acid for the preparation of a pharmaceutical composition for the treatment of brain tumors.

U.S. Pat. No. 6,207,711 describes a photoaging inhibitor comprising one or more compounds selected from triterpenoid derivatives and salts thereof, wherein the triterpenoid derivatives are derived by substituting a functional group for a hydrogen atom in a carboxyl group at the 28-position and/or a hydrogen atom in a hydroxyl group bonded to a carbon atom at the 3-position of ursolic, oleanolic or betulic acid, wherein at least one of the functional groups is a functional group having an aromatic ring.

U.S. Pat. No. 6,323,183 describes methods and compositions for treating Kaposi's sarcoma and Epstein Barr vims using a therapeutic derivative of a triterpenoid acid.

U.S. Pat. No. 6,492,429 describes an osteoarthritis treatment using a composition containing apocynin and an inhibitor of inducible nitric oxide synthase such as curcumin and *Boswellia* extract.

U.S. Pat. Nos. 6,534,086 and 6,949,260 describe a composition for treating inflammation and pain in mammals comprising a boswellic acid, a curcuminoid, a gingered, a capsaicinoid, a bioflavonoid, and a vitamin C source, in various combinations.

U.S. Pat. No. 6,589,516 describes a composition suitable for use on skin or hair comprising: a) at least one extract of a *Boswellia* plant or at least one boswellic acid; and b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms and derivatives of these branched fatty alcohols.

U.S. Pat. No. 6,777,004 describes an anti-fungal oleanane triterpenoid oligoglycoside compound derived from a mangrove plant Aegiceras corniculatum.

U.S. Pat. No. 6,974,801 describes a family of triterpenoid derivatives with various substituents at the C-17 position of 2-cyano-3, 12-dioxooleana-1, 9(11)-dien-28-oic acid. In particular, 2-cyano-3,12-dioxooleana-1,9(11)-dien-28-onitrile, 1-(2-cyano-3,12-dioxooleana-1,9(11)-dien-28-oyl) imidazole, 1-(2-cyano-3,12-dioxooleana-1,9(11)-dien-28-oyl)-2-methylimidazole, 1-(2-cyano-3,12-dioxooleana-1,9 (11)-dien-28-oyl)-4-methylimidazole demonstrated high inhibitory activity against production of nitric oxide induced by interferon-.gamma, in mouse macrophages. The compounds are claimed to be useful in the prevention or treatment of diseases such as cancer. Alzheimer's disease, Parkinson's disease, multiple sclerosis, rheumatoid arthritis, and other inflammatory diseases.

U.S. Pat. No. 7,112,573 describes isoflavonoid and triterpenoid compounds isolated from a soybean phytochemical concentrate. The compounds exhibited cytotoxic activity against selected tumor cell lines.

U.S. Pat. No. 7,195,790 describes compositions derived from extracts from plants in the Asteridae subfamily, such as Carthamus tinctorious, that are effective to selectively inhibit COX-2 activity and/or enhance COX-1 activity. When Asteridae extracts are combined with boswellic acid, the combination exhibits a synergistic inhibitory effect on both COX-2.

U.S. Pat. No. 7,582,314 describes compositions and methods for the management of hyperproliferative skin conditions such as psoriasis. The preferential composition contains a natural leukotriene inhibitor selected from *Boswellia* serrata gum resin, its extractives, isolates or derivatives in combination with a bioavailable organic selenium nutritional supplement.

U.S. Pat. No. 7,645,461 and Application 20060177467 describe mixtures of the hydrogenation products of olibanum for the prophylactic and/or therapeutic treatment of cerebral ischemia, cranial/brain trauma and/or Alzheimer's disease. Compositions comprise pure boswellic acids, tirucallic acids or other triterpenes, and their physiologically acceptable salts.

U.S. Pat. No. 7,811,997 describes compositions containing triterpenoid sapogenins extracted from bamboo. These compositions possess anti-free radical, anti-oxidation, anti-tumor and anti-hypertension functionality. The compositions are used for the treatment or prevention of cardiovascular and cerebrovascular diseases and tumor.

U.S. Application 20020010168, 20050209169 and 20070129317 describe boswellic acid compositions for preventing and combatting diseases which are caused by increased leucocytic elastase or plasmin activity.

U.S. Application 20030195182 describes a triterpene derivative useful for the treatment of hepatic disorders. The described compound comprises as an active ingredient a triterpene derivative containing a hydroxyl group, arylmethyloxy, lower alkoxy, or lower alkanoyloxy, and a lower alkyl, lower alkenyl or formyl which is combined with each other to form oxo, hydroxyimino, or alkylidene.

U.S. Application 20030195367 describes a method for preparing a fatty substance ester, characterized in that it consists in subjecting to an esterification reaction at least a fatty substance with triterpene alcohols and their hydrogenated homologues.

U.S. Application 20030199581 describes enhancing boswellic acids by peracetylation, or peracetylation and mild oxidation to increase the ratio of 3-.beta.-acetyl-11-keto-.beta.-boswellic acid to .beta-boswellic acid, 3-.beta.-aectyl-.beta.-boswellic acid and 11-keto-.beta.-boswellic acid.

U.S. Application 20040073060 describes a process for enriching the 3-O-acetyl-11-keto-.beta.-boswellic acid content of a composition.

U.S. Application 20040151792 describes a natural formulation of compounds to modulate inflammation. The formulation inhibits expression of COX-2, inhibits synthesis of prostaglandins selectively in target cells, and inhibits inflammatory response selectively in target cells. The compositions contain isolates from hops, including tryptanthrin and conjugates, an extract or compound derived from rosemary, a triterpene species, or a diterpene lactone.

U.S. Application 20040166182 describes combinations of extracts from plants in the Asteridae subfamily and extracts from *Boswellia*.

U.S. Application 20050192251 describes a water-soluble bioactive fraction obtained from the gum resin exudate of *Boswellia* serrate and mixtures of potassium and calcium salts of polysaccharides composed of units of arabinose, galactose and D-glucuronic acid. The compositions possess anti-inflammatory and anti-arthritic activities.

U.S. Application 20060073222 describes saponin mixtures and compounds which are isolated from the species *Acacia victoriae*. These compounds may contain a triterpene moiety to which oligosaccharides and monoterpenoid moieties are attached. The mixtures and compounds have properties related to the regulation of apoptosis and cytotoxicity of cells and exhibit potent anti-tumor effects against a variety of tumor cells.

U.S. Application 20060234990 describes a method of treatment of lymphoproliferative and autoimmune disorders with a composition of four boswellic acids including .beta.-boswellic acid, 3-O-acetyl-.beta.-boswellic acid, 11-keto-.beta.-boswellic acid, and 3-O-acetyl-11-keto-.beta.-boswellic acid.

U.S. Application 20060280811 describes combinations of analgesic/anti-inflammatory, immunomodulating and cartilage-reconstructing agents in particular comprising saligenig, boswellic acid, procyanidins, N-acety-glucosamine and either glucoronic acid or glucorenolactone, for the treatment of rheumatoid arthritis.

U.S. Application 20070231345 describes an oral formulation of acetyl-11-keto-beta-boswellic acid in combination with a bioavailable organic selenium supplement dispersed in a pharmaceutical carrier, and a topical formulation of acetyl-11-keto-beta-boswellic acid alone dispersed in a pharmaceutical carrier.

U.S. Application 20070231418 describes a continuous process for obtaining triterpenes from plants and/or their components.

U.S. Application 20070249711 describes natural triterpene compounds that improve brain function.

U.S. Application 20070253943 describes compositions for topical treatment of mammalian skin, to relieve the distressing symptoms of skin diseases and provide, in many cases, a long term core. The composition comprise, in combination, one or more boswellic acids and/or a fatty acid having a chain length of at least 18 carbon atoms and which contains at least two unsaturated linkages together with an enzyme based antibacterial system.

U.S. Application 20070281047 describes a composition which includes a pulp extract from the fruit of Argania spinosa and at least one dermopharmaceutical or cosmetic auxiliary and/or additive. In particular, compositions employing an extract from the fruit of Argania spinosa, and a triterpene fraction of an extract of the pulp of the fruit of Argania spinosa includes lupeol, .alpha.-amyrine, .beta.-amyrine, taraxasterol, and psi-taraxasterol.

U.S. Application 20070299285 describes an oleogel-forming agent comprised of at least one highly dispersed triterpene.

U.S. Application 20080003639 describes a sequence which corresponds to a soybean-derived cytochrome P-450 gene that encodes an enzyme protein that carries out hydroxylation of the 24-position of an oleanane type triterpene and uses for such triterpenes.

U.S. Application 20080020998 describes sustained-release compositions that comprise effective amounts of glucosamine, curcuminoids, boswellic acids and piperine.

U.S. Application 2008011942 describes triterpene saponins isolated from the root of Ilex pubescens. The chemical structures and some properties of the triterpene saponin fraction exhibits anti-inflammatory and analgesic activity.

U.S. Application 20080206169 describes *boswellia* compositions comprising at least one skin care active selected from the group consisting of acetyl glutamic acid, acetyl glutamine, acetyl methionine, acetyl tributyl citrate, acetyl triethyl citrate, acetyl tyrosine, adipic acid, alanine, arginine, arginine glutamate, benzophenone-3, camphor, gluconolactone, glucose, glycine, histidine hydrochloride, hydroxyproline, maltitol, phenylalanine, succinic acid, buffered lactic acid, tris(tetramethylhydroxypiperidinol) citrate.

U.S. Application 20080275117 describes compositions of alpha.- and/or .beta.-boswellic acid and/or their C-acetates.

U.S. Application 20080280839 describes Androsace umbellata Merr. extract having anticancer activity and a triterpene saponin compound isolate. In particular, isolates of saxifragifolin B and saxifragifolin D, which inhibits the growth of cancer cells and induces apoptosis of cancer cells, and thus are useful for preparing a composition for preventing and treating cancers.

U.S. Application 20080317885 describes compositions comprising a curcuminoid, a polymethoxylated flavone, a catechin, and a boswellic acid. These compositions are useful for the treatment of Alzheimer's disease, atherosclerosis, arteriosclerosis, osteoarthritis and other degenerative joint diseases, Huntington's chorea, Parkinson's disease, optic atrophy, retinitis pigmentosa, macular degeneration, muscular dystrophy, aging-associated degenerative processes, asthma, dermatitis, laminitis, pemphigoid, pemphigus, reactive airway disease, inflammatory bowel disease (e.g., Crohn's disease, ulcerative colitis), multiple sclerosis, rheumatoid arthritis, periodontal disease, systemic lupus erythematosus, sarcoidosis, psoriasis, type 1 diabetes, ischemia-reperfusion injury, chronic inflammatory diseases, geriatric wasting, cancer cachexia, cachexia associated with chronic inflammation, sick feeling syndrome, and other inflammatory and/or degenerative diseases, disorders, conditions, and processes in humans and other animals.

U.S. Application 20080317886 describes compositions of *Boswellia* extract comprising additionally any or all of high-glycemic sugars and/or polysaccharides (e.g., sucrose, glucose, maltodextrin), all essential amino acids and beta-hydroxy-beta-methylbutyrate and can include other amino acids sources (e.g. whey protein), performance enhancing agents (e.g., caffeine, L-glutamate), anti-inflammatory agents (e.g., ginger, *boswellia*, curcumen), antioxidants (vitamin C, vitamin E, selenium, polyphenols,), insulin-mimicking agents (cinnamon, Banaba), and analgesics (e.g. aspirin, ibuprofen, naproxen, acetaminophen).

U.S. Application 20090042832 describes salts or ion pair complexes obtained by a reaction between boswellic acids or selectively enriched 3-O-acetyl-11-keto-.beta.-boswellic acid (AKBA) or 11 keto-.beta.-boswellic acid (KBA) and an organic amine, more particularly with glucosamine.

U.S. Application 20090136566 describes compositions of triterpenes isolated from Birch bark.

U.S. Application 20090169651 describes compositions comprising the extract from the liquid endosperm of Cocos nucifera as the principle ingredient along with one or more actives including the fruit rind extracts of Garcinia cambogia, Garcinia indica and Garcinia mangostana, seed coat extract of Tamarindus indicus, Chlorogenic acid extract from the beans of Coffea arabiea, seed extracts of *Nelumbo* species, the leaf extracts of Murraya koenigii and the triterpene pentapeptides of oleanolic acid and ursolic acid.

U.S. Application 20090186837 describes compositions comprising triterpene glycosides.

U.S. Application 20090263512 describes compounds comprising at least one sugar, a triterpene, such as Sapogenin, and at least one side chain at Carbon 21 and 22, such as Angcloyl groups.

U.S. Application 20090264377 describes compositions containing a triterpene glycoside.

U.S. Application 20090298938 describes compositions of triterpenoic acids.

U.S. Application 20100098676 describes compositions comprising enriched 3-O-acetyl-11-keto-.beta.-boswellic acid and enriched demethylated curcuminoids.

U.S. Application 20100098786 describes a formulation comprising eicosapentaenoic acid, or an ester thereof, and a triterpene, or art ester thereof, and the use of such a formulation.

U.S. Application 20100099763 describes various triterpene compounds.

U.S. Application 20100166670 describes compositions of boswellic acid.

U.S. Application 20100189824 describes combinations of a triterpene moiety to which oligosaccharides and monoterpenoid moieties are attached U.S. Application 20100190968 describes oleanane-type triterpene saponin compounds, which are effective for improving memory and learning ability U.S. Application 20100209388 describes a nutraceutical composition containing boswellic acid.

U.S. Application 20100267983 describes water-soluble triterpenephenol compounds having antitumor activity.

U.S. Application 20110015196 describes lupeol-type triterpene derivatives and related compounds, and pharmaceutical compositions useful for therapeutic treatment of viral diseases and particularly HIV mediated diseases.

U.S. Application 20110054025 describes compositions of oleanolic acid (3.beta.-hiydroxyolean-12-en-28-oic acid), a pentacyclic triterpene.

U.S. Application 20110077227 and 20110077228 describe 21-keto triterpene compounds.

U.S. Pat. No. 5,268,178 describes methods that involve the use of biodegradable antibiotic implants which are placed in a surgical void and then supply an extended, continuous supply of at least one antibiotic to the surrounding tissue. The biodegradable implant comprises at least one biodegradable material such as polylactic acid, and at least one antibiotic drug.

U.S. Pat. No. 5,411,737 describes a slow release drug delivery device for the prolonged administration of topically active medicines which consists of a vehicle in which water is soluble and in which is dissolved the topically active drug which is formed into a stable organogel with a polymer matrix with a very low water absorbing capability.

U.S. Pat. No. 5,571,080 describes surgical dressing in which the composition takes the form of a drug coaled water-absorbing and water-swellable hydrocolloid material distributed throughout the interstices of a three-dimensional, open-mesh, randomly-oriented network of flexible, water-insoluble, polymeric filaments, such filaments being surface coated by a tacky, water-insoluble adhesive material that has an adherence.

U.S. Pat. No. 5,869,079 describes a drug release device comprised of combinations of hydrophilic and hydrophobic entities in a biodegradable sustained release implant with adjustable rate of release.

U.S. Pat. No. 5,947,893 describes medical devices having at least one porous tissue-mating surface. The tissue-mating surface of the device includes therein a pharmacologically active substance within a biodegradable carrier, such as a polymer or a biodegradable ceramic, such as calcium phosphate.

U.S. Pat. No. 6,022,554 describes coating formulations for coating sustained-release drug implants. The coating formulations are capable of forming a porous film coat over a biologically active agent to provide a release of the active agent at a constant rate over a prolonged period of time.

U.S. Pat. No. 6,703,047 describes compositions and methods for forming tissue-adherent hydrogels containing drugs using substantially dry precursors.

U.S. Pat. No. 5,676,967 describes a wound dressing for covering a wound to the body, providing slow release of a combination of collagenic protein and oligosaccharide, enhancing vapor transmission from the wound, and enhancing healing with an aqueous combination of collagen and oligosaccharide coated on a mesh surface and dehydrated to a low moisture content.

U.S. Pat. No. 6,872,225 describes an implant having a coating comprising a polymer matrix swollen in a pharmaceutical solution whereby pharmaceutically active compound is imbibed into the polymer matrix. When the product is implanted, release of the pharmaceutically active compound from the coaling takes place. The polymer is preferably formed from ethylenically unsaturated monomers including a zvvitterionic monomer, most preferably 2-methacryloyloxyethyl-2'-trimethylammoniumethylphosphate inner salt.

U.S. Pat. No. 7,153,520 describes a composition for the sustained delivery of a drug comprising an amphiphilic diblock copolymer; a poorly water-soluble drug; a biodegradable polymer; and liquid poly(ethylene glycol) or functional derivatives thereof and a process for preparing the composition.

U.S. Pat. No. 7,438,925 describes drug eluting coating compositions composed of at least one therapeutic agent dispersed in modified, biologically active binders. The therapeutic agents included in the coating composition are paclitaxel, sirolimis, tacrolimus, everolimus, actinomycin-D, dexamethasone, mycophenolic acid, cyclosporins, estradiol, and derivatives and analogs thereof.

U.S. Pat. No. 7,741,273 describes a method for alleviating pain associated with neuromuscular or skeletal injury or inflammation by targeted delivery of one or more therapeutic agents to inhibit the inflammatory response which ultimately causes acute or chronic pain.

U.S. Pat. No. 7,749,539 describes poly(ester-anhydrides) or polyesters formed from ricinoleic acid and natural fatty diacids and their method of preparation and its use for delivering bioactive agents including small drug molecules, peptides and proteins, DNA and DNA complexes with cationic lipids or polymers or nano and microparticles loaded with bioactive agents U.S. Pat. No. 7,754,272 describes an implant having a coating comprising a polymer matrix is swollen in a pharmaceutical solution whereby pharmaceutically active compound is imbibed into the polymer matrix.

U.S. Pat. Nos. 7,842,303 and 7,858,110 describe use of polyurethane based polymer as a drug delivery device to deliver biologically active compounds at a constant rate for an extended period of time and methods of manufacture.

U.S. Pat. No. 7,919,112 describes methods and compositions of tissue, fixed using polymeric and/or variable length crosslinks, and di- or polymercapto compounds. Also described are the methods and compositions wherein the tissue is fixed using biodegradable crosslinkers forming a membrane-like implantable tissue to make an implantable drug delivery patch U.S. Application 20050281860 describes an anti-proliferative drug, such as rapamycin or taxol, placed onto or within a sheet of material or mesh. The strands onto or into which the drug is placed may be either a permanent implant or it may be biodegradable.

U.S. Application 20060251702 describes a prosthetic tissue support mesh, and especially such a mesh comprised of a remodelable material that promotes tissue ingrowth, incorporates an effective amount of an anti-inflammatory compound such as a non-steroidal anti-inflammatory drug (NSAID) to inhibit the formation of tissue adhesions to the mesh and/or to surrounding tissues when implanted in a patient.

U.S. Application 20070155906 describes a biodegradable multi-block copolymer, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous at physiological (body) conditions.

U.S. Application 20070299285 describes an oleogel-forming agent which comprises at least one highly dispersed triterpene. The invention also relates to an oleogel which comprises a nonpolar liquid in an amount ranging from 80% by weight to 99% by weight based on the total weight of the oleogel and an oleogel-forming agent comprising a highly dispersed triterpene.

U.S. Application 20080118550 describes a surgical mesh formed of a biocompatible mesh structure with a coating that provides anti-inflammatory, non-inflammatory, and anti-adhesion functionality for an implantation in a patient. The coating is generally formed of a fish oil, can include vitamin E, and may be at least partially cured.

U.S. Application 20090018559 describes surgical meshes coated with one or more biodegradable polymers that can act as a stiffening agent by coating the filaments or fibers of the mesh to temporarily immobilize the contact points of those filaments or fibers and/or by increasing the stiffness of the mesh.

U.S. Application 20090099600 describes a polyurethane or polyurethane/urea composition providing a drug delivery coating.

U.S. Application 20090263460 describes an implant designed as a drug loaded polymer device, preferably a biodegradable polymer, such as poly(lactide-co-glycolide) or polylactic acid/polylactide.

U.S. Application 20090281558 describes implantable medical articles which comprise a surgical mesh that is at least partially covered.

U.S. Application 20090292013 describes a composition, comprising a thermoplastic polymer, a rate modifying agent and a biologically active agent, useful as a slow-release drug-delivery implant in the body of a human.

U.S. Application 20100098786 describes a formulation comprising eicosapenaenoic acid, or an ester thereof, and a triterpene, or an ester thereof, and the use of such a formulation.

U.S. Application 20110135703 describes a synthetic mesh, an allograft, or a xenograft containing antimicrobial material as a coating. The coating of the material is performed either by adsorption or by covalent bonding.

In view of the present art, it is desirable to provide methods and compositions resulting therefrom that enhance, augment and facilitate the biological activity of plant substances and their synthetic analogs. In what follows, compositions derived from extracts of *Boswellia* will be cited, but it is understood the methods described are applicable to any biologically active substance with a hydroxyl group, and in particular plant substances with an available hydroxyl group.

It is one object of the present invention to alter the hydrophilicity of boswellic acid fractions to make them more compatible with substances residing in the body. Compositions comprising boswellic acids can desirably be made more compatible with lipids by making them more hydrophobic, for use in situations in which it is desirable to deliver boswellic acids through the skin, for example. In other situations, it can be desirable to modify the boswellic acid fractions to be more hydrophilic, so that they will readily disperse in a hydrophilic environment. In other instances, it may be desirable to employ a mixture of hydrophobically modified and hydrophilically modified boswellic acids, such that when applied to skin, some are surface acting and others are skin penetrating.

It is another object of the present invention to attach hydrophilic polyethylene glycol to boswellic acid fractions and their salts to increase their hydrophilicity.

It is another object of the present invention to attach hydrophobic polypropylene glycol to boswellic acid fractions and their salts to increase their hydrophobicity.

It is another object of the present invention to attach amphiphilic polyol comprised of block units of polyethylene oxide and polypropylene oxide to boswellic acid fractions and their salts to make certain regions of a therapeutic molecule hydrophobic and other regions of the same molecule hydrophobic. For example, one of the causes of skin drying and ageing is a reduction in the amount of lipid contained within intercellular lipid lamella of the stratum corneum. The aggregation of amphiphilic molecules into micelles, bilayers, vesicles and more generally biological membranes make amphiphilic molecules suitable for forming a bilayer within tissue. Such molecules possess a polar head group and at least two hydrocarbon chains, such that there exists a clearly defined relationship between the volume occupied by the hydrocarbon chains and the optimum area occupied by the polar head group.

It is another object of the present invention to attach polyol to triterpene glycyrrhetinic acid to enhance their anti-ulcer, anti-inflammatory, anti-allergic, anti-hepatitis and antiviral actions. In particular, the modification of carbenoxolone, glycyrrhetinic acid ester derivatives having substituents at the 3' position, amino acid salts of glycyrrhetinic acid, amide derivatives of glycyrrhetinic acid, and amide derivatives of 11-deoxoglycyrrhetinic acid.

It is another object, of the present invention, to attach polyol to betulinic acid, a pentacyclic triterpene, to enhance it as an inhibitor of human melanoma tumor growth.

It is another object of the present invention to attach polyol to triterpene saponins from a Chinese medicinal plant in the Cucurbitaceae family to enhance its antitumor activity It is another object of the present invention to attach polyol to monoglycosides of interpenes to enhance its selective cytotoxicity against MOLT-4 human leukemia cells.

It is another object of the present invention to attach polyol to six triterpenoic acids namely B-Boswellic acid (3a-hydroxy urs-12 ene-24-oic acid); acetyl B-boswellic acid (3a-acetoxy urs-12-ene-24-oic acid)I; 11-keto-B-boswellic acid (3a-hydroxy urs-12-ene-11-keto-24-oic acid); acetyl 11-keto-B-boswellic acid (3a-acetoxy urs-12-ene-11-keto-B-boswellic acid), 3a-hydroxy urs-9, 12-diene-24-oic acid, 2a, 3a dihydroxy urs-12-ene-24-oic acid, together with other unidentified compounds.

It is another object of the invention is a method of enhancing the dual pharmacophoric activity of a triterpenoid compound consisting of binding a polyol, directly or indirectly, to the 3 position of the triterpenoid.

It is another object of the present invention to link the polyol and triterpenoid compound via an enzymatically cleavable linker. Such a link would degrade in the body, releasing an unmodified form of the triterpenoid. Such a link could be a urethane or urea link. A preferred linker of this sort would be cleavable by enzymes present in significant levels at the disease site. For example, if it is desired to target the invention compounds and drug to a site of inflammation, an enzymatically cleavable linker would be chosen that is cleaved by enzymes produced and secreted by inflammatory cells thereby causing the release of the compound and drug at the site of inflammation, in particular, reactive oxygen species are typically associated, with inflammation, and these and other links are susceptible in this environment.

It is another object of the present invention to deliver cytotoxic substance by an enzymatically cleavable linker connecting a long polyethylene glycol to the cytotoxic substance derived from *Boswellia*. Long polyethylene glycol chains reduce the toxicity of many substances when attached. This means of boswellic acid delivery would significantly reduce systemic effects associated with compounds that display toxicity when administered in free form but not as part of a conjugate.

It is another object of the present invention to utilize the polyol addition as a means to attach other drugs beneficially associated with boswellic acid, for example but is not limited to, simple polymers, polymeric carbohydrates, including cyclodextrins, heparin or its derivatives, peptides, etc.

The affinity of boswellic acid fractions for a selectin receptor can be enhanced by providing multiple copies of a desired fraction its close proximity, preferably using a multi-armed structure provided by a polyol moiety. Such multiple arm structure end capped with boswellic acid with optimal spacing between the boswellic acids can dramatically improve binding to a receptor, the multivalency and spacing can be controlled by selection of a suitable molecular weight polyol with suitable OH number. Such moieties can be functionalized with diisocyanate groups, or other functional groups, capable of linking to the hydroxyl groups of the polyol and presenting a multiplicity of functional NCO groups that can be reacted with hydroxyl groups associated with the compounds extracted from *Boswellia*.

In still yet another aspect of the invention, topilogical compositions are provided which comprise one or more, including any possible combination thereof, of the compounds provided by the invention. Such a topical composition may comprise a cosmetically acceptable medium, for example, a buffer, a solvent, a diluent, an inert carrier, oil, or a créme.

In still yet another aspect, a method is provided of inducing apoptosis in a cell comprising contacting said cell with a therapeutically effective amount of the compositions of the present invention. In one embodiment of the invention, the cell may be a mammalian cell, and/or a malignant cell, and may be further located in a human. In the method, contacting may comprise administering said composition to a human. Such administration may be by any method, including oral, topical, and intravenous, via intratumoral injection and by inhaling air aerosol. In certain embodiments of the invention, the cell is a skin cell, a colon cell, a uterine cell, an ovarian cell, a pancreatic cell, a prostate cell, a renal cell, a lung cell, a bladder cell or a breast cell. The method may further comprise administering at least a second pharmaceutical composition and/or may comprise irradiating the cell, for example, with X-ray radiation, UV-radiation, .gamma.-radiation, or microwave radiation.

The inventors specifically contemplate further uses of the compounds of the invention for a range of applications in addition to the inhibition of tumor cell growth. For example, the compounds of the invention may, in certain aspects of the invention, find use as anti-fungal and anti-viral agents, piscicides or molluscicides, contraceptives, antihelmintics, UV-protectants, expectorants, diuretics, anti-inflammatory agents, regulators of cholesterol metabolism, cardiovascular effectors, anti-ulcer agents, analgesics, sedatives, immuno-modulators and antipyretics.

The compounds of the invention may further find use in the regulation of angiogenesis. Angiogenesis or neovascularization is defined as the growth of new blood vessels. Tumors and cancers induce angiogenesis to provide a lifeline for oxygen and nutrients for the tumor to thrive. The development of new blood vessels also provides exits for malignant cancer cells to spread to other parts of the body. Angiogenesis inhibition therefore benefits cancer patients. Angiogenesis also is required at times such as wound healing. These wounds can be external wounds or internal organ wounds that result from accidents, burns, injury and surgery. Thus, agents that promote angiogenesis have a great potential for use in therapy for wound healing.

The application of the compounds of the invention for modulation of cholesterol metabolism is also contemplated. For example, certain saponins are known to have the effect of lowering the serum cholesterol levels of human patients. Therefore, by treating patients with the triterpene saponins, either orally or intravenously, the morbidity associated with high cholesterol and related cardiovascular diseases may be decreased. Further, for the treatment of cardiovascular conditions, it is contemplated that the compounds of the invention may be used for the treatment of arrhythmic action and further may be used as a vascular relaxant, resulting in an antihypertensive activity.

Another potential application of the compounds of the invention is as an anti-inflammatory agent. Significantly, recent evidence suggests the involvement of the inflammatory response in carcinogenesis. Treatment of patients with the compounds of the invention may, therefore, potentially alleviate a wide degree of ailments associated with inflammation, including tumorigenesis and tissue damage. Such stages of inflammation that may be affected include increased blood vessel permeability and release (exudation) of histamine, serotonin and basic polypeptides and proteins, accompanied by hyperaemia and oedema formation, as well as cellular infiltration and formation of new conjunctive tissue.

Further use may be found as ingredients in topical agents, for example, as agents for protection from skin aging and/or carcinogenesis, whether due to endogenous or external factors, for example, a suitable application comprises the use of the compounds of the invention as an ingredient in sunblock, or other similar lotions for application to human skin. The potential benefit of such a composition is indicated by the anti-tumor activities identified herein for certain of the compounds of the invention. Such lotions and sunblocks containing the compounds of the invention may, therefore, be particularly suited to those with a predisposition to various forms of ski n damage or cancer, including the fair skinned or those with a genetic predisposition to skin cancer.

Other possible applications of the compounds include use as an antioxidant, for modulating production of nitrous oxide in cells, for protection of the central nervous system from damage, and for the treatment of hypertension or atherosclerosis. In addition, the inventors specifically envision the topical application of the compounds of the invention for enhanced penile function.

In consideration of the related art concerning devices, it is an object of this invention to have a sheet of material that can be placed between internal body tissues, the material having a triterpene composition attached to reduce the incidence of infection and severity of inflammation between adjacent layers of the human tissue.

Another object of this invention is to have a biodegradable sheet of material or mesh suitable for placement between body tissues including an attached triterpene composition that prevents the cellular proliferation associated with post-surgical adhesions.

Still another object of the invention is to employ a device placed into or onto the body of a human subject, which device has an attached tripertene composition, plus using the same or a different triterpene composition as a medication to be applied systemically to the human subject from a time prior to a surgical procedure to a time after that procedure.

SUMMARY OF THE INVENTION

Compositions of botanical extracts having enhanced biological activity are pro vided by polymerizing a polyol with a plant fraction containing hydroxyl groups in the presence of a nitrogen containing atmosphere free of water. In particular, *Boswellia* acidic fractions are polymerized with multifunctional polyols to enhance their biological activity and transport into tissue.

Compositions of the present invention derived from boswellic acids can desirably be made more compatible with lipids, for use in situations in which it is desirable to deliver boswellic acids through the skin. In oilier situations, it can be desirable to have the boswellic acid modified to disperse more readily in a hydrophilic environment. Modification according to the present invention of boswellic acids can be useful, especially if the solubility of the modified boswellic acid is sufficiently high to provide an effective concentration of the phytochemical. Additionally, solubility of modified boswellic acid preparations can be increased using a solubility enhancing agent, such as propylene carbonate.

Compositions of the present invention derived from boswellic acids can be made more hydrophobic by attaching a polyol wherein the predominant monomeric unit is propylene oxide. The polyol can be linked to the hydroxyl group of the boswellic acid via a urea link or urethane link. Generally, a diisocyanate is used to link the polyol and boswellic acid fraction.

A diisocyanate can be polymerized to the hydroxyl group on the boswellic acid to form a urethane link between the diisocyanate and the boswellic acid. The resulting isocyanate functionalized boswellic acid will then polymerize with the hydroxyl group of a polyol forming an additional urethane link. Alternatively the polyol may be isocyanate functionalized, and then reacted with the hydroxyl group of the boswellic acid. Alternatively, both polyol and boswellic acid may be isocyanate functionalized, and these mixed with a stoichiometric amount of water to form urea links between the boswellic acid and polyol.

Diisocyanates are generally hydrophobic, but their hydrophobicity can be counteracted by the attachment of a hydrophilic polyol. However, in the case of desiring a hydrophobic composition, some diisocyanates are more hydrophobic than others, and this knowledge can be used to enhance or decrease the hydrophobicity of the product.

Compositions of the present invention derived from boswellic acids can be made more hydrophilic by attaching a polyol wherein the predominant monomeric unit is ethylene oxide. The polyol can be linked to the hydroxyl group of the boswellic acid via a urea link or urethane link. Generally, a diisocyanate is used to link the polyol and boswellic acid fraction in the variety of ways indicated above for hydrophobic products.

It has been recognized that it would be advantageous to develop an implantable or indwelling device for the sustained delivery of a triterpeneor modified triterpene that is capable of releasing or presenting the therapeutic when administered into a particular body site.

The present invention provides a composition for the sustained delivery of these triterpenes when administered info a particular body site and the triterpene and polymeric matrix containing the triterpene are slowly released, in vivo, from the implant.

A first embodiment of this invention is a device consisting of a drug impregnated into, coated onto or placed onto a material sheet or mesh designed to be placed between internal body tissues that have been surgically separated to prevent the formation of post-operative adhesions. A triterpene that is impregnated into a smooth sheet of material or coated onto the material or joined to the material by adhesion, bonding and/or absorption is defined herein as a triterpene "attached" to a surgical barrier.

This sheet onto which the triterpene is attached may be either a permanent implant or it may be preferably biodegradable. The triterpene can be attached to an existing product such as the MAST Biosurgery SurgiWrap™ absorbable surgical barrier. Triterpenes possess many beneficial attributes, including anti-microbial activity, wound healing promotion, and anti-inflammatory effects. Chronic inflammation has been associated with tissue adhesions between a tissue repair and surrounding tissue. It is beneficial to combine a medical implant such as a surgical barrier with triterpenes and their derivatives.

The sheet onto which the triterpene is attached can be comprised of biodegradable polymeric compositions which may include organic esters or ethers, which when degraded result in physiologically acceptable degradation products, including the monomers. Anhydrides, amides, orthoesters or the like, by themselves or in combination with other monomers, may find use. The polymers are preferably condensation polymers. The polymers may be cross linked or non-cross-linked, usually not more than lightly cross-linked, generally less than 15%, usually less than 5%. For the most part, besides carbon and hydrogen, the polymers will include oxygen and nitrogen, particularly oxygen in a polyether or nitrogen in a polyurethane. The oxygen may be present as propylene oxide, and polymerized forms. The nitrogen may be present as urea, urethane, amide, cyano and generally amino.

The biodegradable surgical barrier would decrease the incidence of infection and inflammation and hence be a deterrent to the formation of adhesions. Similarly, it is also envisioned that a triterpene composition attached to a bandage could be placed onto a cut in the skin for reducing infection and scar tissue formation. The tissue defect could be accidental or a result of a surgical incision.

It is also envisioned that a triterpene composition could be attached to surgical suture material that is used (for example) to join together two blood conducting cylindrical cavities, i.e., an anastomosis, with the attached triterpene causing a reduction in cellular proliferation in the vicinity where the sutures penetrate through the human tissue. It should be understood that the suture material could be either soluble or insoluble and could be used for any application for which sutures are used.

Still another embodiment of the present invention is a triterpene composition coated onto a surgical staple thus reducing scar tissue around that staple.

Still another embodiment of this invention is to attach a triterpene composition to a device such as a soft tissue reconstructive mesh that is used for the treatment of a hernia. Since scar tissue formation is one of the main complications of hernia repair, by attaching a triterpene composition to a mesh that is placed over a tissue defect, there can be some reduction in adhesion severity and incidence.

It is also envisioned to attach a triterpene composition attached to the outside of a cylindrical lube that is placed within a generally cylindrical cavity of the human body to decrease scar tissue formation and infection after a surgical procedure. Such a generally cylindrical cavity might be a nostril after an operation for a deviated septum, a fallopian tube, a billiary duct, a urethra, (for example after prostate surgery) a ureter, a bronchial tube, etc. For such an application, the tube with the attached triterpene composition could be biodegradable, remain implanted or it could be removed after a few days or weeks.

One aspect of the present invention relates to joining a triterpene composition to a medical device. According to the present invention, a polylactic acid polymer or polylactic acid polyurethane copolymer when mixed with a solution of polyether modified triterpene forms polymeric micelles in a liquid of polymer dissolved in an organic solvent. As the solvent is driven off, a smooth solid polymer sheet is formed and the triterpene composition is trapped within the polymeric micelles. In addition, when administered into the body, the biodegradable aspect of the polymer causes the triterpene composition to slowly release in vivo from the implant matrices over sustained periods of time and the polymers then decompose into materials harmless to the human body.

The polylactic acid polyurethane copolymer in the present invention is preferably a well distributed random block copolymer of a hydrophilic poly(alkylene glycol) blocks and a hydrophobic polylactic acid blocks dispersed such that the polymeric ends are randomly hydrophilic and hydrophobic. Furthermore, the distribution of blocks is such that as the implant degrades there is not formed macroscopic fragments of substantially hydrophobic polymer.

The term poly(ethylene glycol) or PEG, as used herein, shall also be deemed to include derivatives of PEG unless otherwise specifically stated. Derivatives include multi-functional PEGs containing greater than 2 hydroxyl groups per molecule. Such derivatives will be more specifically described in the disclosure that follows.

Since only the hydrophilic component block, not the hydrophobic component block, of the copolymer has an affinity or attraction for tissue, the block copolymer forms a core-shell structure wherein the relatively more hydrophobic triterpene composition occupies the inner core and the molecules of the copolymer orient in liquid phase such that the hydrophobic polylactic acid block forms the outer shell in the copolymer medium, with the hydrophilic poly(ethylene glycol) blocks oriented to the implant surface and toward tissue. In addition, the biodegradable copolymer employed in the present invention may be multi-functional such that it forms networks capable of controlling the release rate of the hydrophobic triterpene and the triterpene containing polymeric micelles.

Alternatively, the polymeric carrier could be entirely hydrophobic, such as comprised of polyiactic acid, and the triterpene composition dissolved into the polymeric carrier. The triterpene composition could be dissolved after the polymeric carrier is formed into a solid sheet or dispersed into the polymeric carrier in a solvent phase and later the solvent driven off.

The content of the triterpene is preferably within the range of 0.1 to 50% by weight and more preferably from 1 to 10% by weight, based on the total weight of the composition. The molecular weight of the biodegradable polymer is within the range of 500 to 5,000,000 Daltons and is preferably from 1,000 to 50,000 Daltons. The polydispersity of the biodegradable polymer is preferably as small as possible and Gaussian, in particular less than 10,000 Daltons.

The implants may be monolithic, i.e., having the active agent homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type may be of benefit in some circumstances, where the therapeutic level of the drug falls within a narrow window. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, case of encapsulation, a half-life in the physiological environment of at least 7 days, preferably greater than 1 month, water insoluble, and the like. The triterpene will usually comprise at least about 0.1, more usually at least about up to 10 weight percent of the implant.

The compositions of the present invention are to be formed as implants to be administered into a particular body site, and the triterpene and polymeric micelles containing the same are slowly released therefrom. Therefore, a constant concentration of the triterpene is kept at the administration site as well as in the circulation thereby achieving excellent pharmacological effects. Also, no organic solvent harmful to the human body is retained in the medical device. Moreover, the polymers employed in the present invention are safely degraded into products harmless to the human body and are then excreted.

Additional features and advantages of the invention will be apparent from the detailed description which follows, taken in conjunction with the accompanying drawings, which together illustrate, by way of example, features of the invention.

DETAILED DESCRIPTION

Methods of Extraction and Purification

Figure 1:
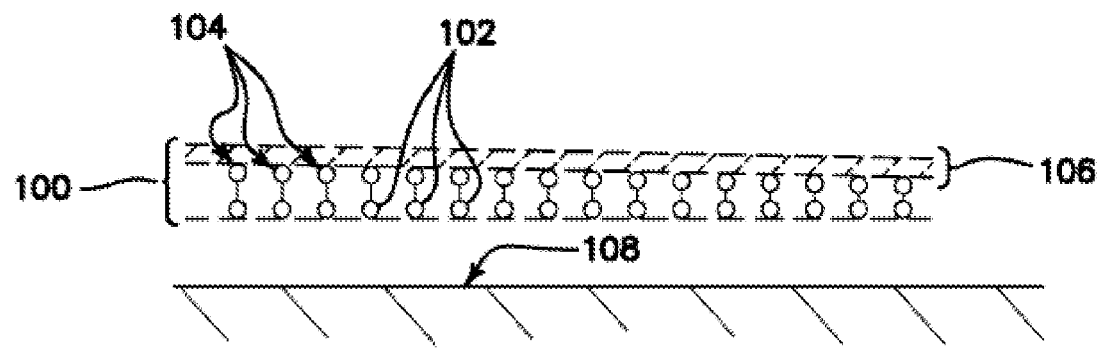
FIG. 1 is a schematic representation of the composition of hydrophilic and hydrophobic structure of the present invention.

The extraction methods described are examples employing *Boswellia* extracts, and are not meant to limit the preparation of other phytochemical extracts using site modification methods described herein.

In a first step, the extract maybe taken up in a convenient polar solvent, e.g. acetone and colored materials and adsorbing materials present in the extract removed. Various conventional absorbents may be used, such as activated charcoal, diatomaceous earths, etc. Mild conditions are employed, conveniently 15 to 35.degree. C. The absorbents are then removed, e.g. filtration, the solution extracted with aqueous base, particularly a mild base with a pH below about 9, the aqueous layer isolated and acidified in the presence of a polar organic solvent that is substantially immiscible with water. After removing the organic solvent by evaporation under a vacuum, the extract maybe further purified by passing through a silica column.

A variety of other solvents may be used, for example ether, and more specifically, cyclic ether, alkyl ether, such as diethyl ether, or alkyl tert-butyl ether such as methyl tert-butyl other. Although a number of organic solvents can be used, in some situations, it can be desirable to use solvents that have relatively low volatility, compared for example with dimethyl ether. In some cases the solvent is not removed from the extracts, for example propylene carbonate. More preferably, a volatile solvent is used in conjunction with a non-volatile solvent, for example propylene carbonate and tetrahydrofuran.

A typical extraction procedure comprises;

(a) crushing the lumps of the gum resin of *Boswellia* and extracting the crushed lumps with a polar solvent to provide an extract;

(b) removing insoluble material from said extract;

(c) concentrating the extract:

(d) basifying the extract with an aqueous solution of an alkali to provide a solution having a pH in the range of 9 to 10;

(e) extracting the solution with chlorinated or non-polar solvents to provide an aqueous layer, and acidifying the aqueous layer with mineral acid to a pH in the range of 3-5 to provide a precipitate comprising boswellic acids;

(f) washing the precipitate with water to provide said fraction being neutral to litmus;

(g) drying the fraction to provide a dry fraction; and, optionally, dissolving this dry fraction in a carrier.

In a preferred method of extraction, the above product, of step (c) was dissolved in a 20 mmolar solution of sodium hydride (611 mg, 25.2 mmole, 6.00 mmole equiv.) in anhydrous tetrahydrofuran (30 mL) at ambient temperature. Sodium iodide (25 mmole) solution and tetrabutylammonium iodide (0.5 mmole) were added and the reaction contents were warmed to a gentle reflux for 60 minutes. The reaction was terminated by the careful addition of 50% methanol in toluene and then 1M hydrochloric acid was added until the pH was 1-2 and then diluted with chloroform. The heterogeneous layers were separated and the organic phase was washed twice with portions of 1M hydrochloric acid and sodium bicarbonate solution. The crude product was dried over anhydrous sodium sulfate and filtered. The solvent was removed in vacuo which produced oil.

Methods of Modification of an Extract

The modification methods described are examples employing *Boswellia* extracts, and are not meant to limit the preparation of other phytochemical extracts using the modification methods described herein.

The present invention provides a medical preparation containing one or more compounds selected from triterpenoid derivatives and salts thereof, wherein the triterpenoid derivatives are derived by substituting an isocyanate functional group fora hydrogen atom in a hydroxyl group of B-Boswellic acid (3a-hydroxy urs-12 ene-24-oic acid; 11-keto-8-boswellic acid (3a-hydroxy urs-12-ene-11-keto-24-oic acid); 3a-hydroxy urs-9,12-diene-24-oic acid; and 2a, 3a dihydroxy urs-12-ene-24 oic acid, wherein at least one of the functional groups is a functional group having an aromatic ring. A specific example of the functional group having an aromatic ring is toluene diisocyanate.

In addition to extracts obtained from plants, the triterpenoids can be produced by chemical synthesis and there is no limitation to use of the triterpenoids obtained synthetically. Therefore, any suitable methods may be selected for the production method of producing the triterpenoids used as a starting material.

In one example, a polyol diisocyanate is synthesized by the reaction of toluene diisocyanate with a diol comprised of 25% propylene oxide and 75% ethylene oxide in a ratio that endcaps all the hydroxyl groups on the polyol with isocyanate groups without chain extension. To avoid chain extension, it is important to dry the polyol in vacuo at 60° C. for 24 hours. The reaction is to be conducted under an atmosphere of dry argon, or other inert gas. The resulting polyol diisccyanate is reacted with a low molecular weight triol, such as trimethylolpropane, to produce a polyol triisocyanate. It is not necessary that every polyol diisocyanate react with a triol, accordingly, the reaction product may be a mixture of polyol diisocyanate and polyol triisocyanate. It is also not necessary to avoid higher order structures, such as polyol 4-isocyanate and higher.

To this product is added the triterpenoids under a nitrogen containing atmosphere. For example, the atmosphere may be 90% nitrogen and 10% nitric oxide. The reaction is begun at room temperature until the exotherm ceases. Then the temperature of the reaction is increased in 5° C. increments taking care to hold the temperature at any point where the exotherm resumes. The mixture should finally be reacted at 60° C. until all the isocyanate functionality is consumed.

Alternatively, the triisocyanate preparation described above may be diluted with 50% by volume of propylene carbonate before the triterpenoids are introduced, or propylene carbonate may be used in any ratio where a desired reaction viscosity is obtained. The amount of propylene carbonate will depend to some degree on the molecular weight of the polyol diols and degree of trifunctionality in the synthesized triisocyanate product.

Alternatively, rather than trimerizing polyol diols, one may obtain commercial triols which then can be endcapped with a diisccyanate.

Forms of Modified Phytochemicals

For medical use, the subject compositions may be formulated in a variety of ways depending on the manner of administration and therapeutic purpose. The composition maybe used as the acid or as a physiologically acceptable salt, such as ammonium, an amine, amino sugar, sodium, potassium, calcium, etc. For a pharmaceutical preparation for oral administration, the product maybe formulated as a tablet or capsule. Various pharmaceutically acceptable additives may be used to obtain particular characteristics for the product. Binding agents include polyvinylpyrrolidone, hydroxypropylmethycellulose, methylcellulose, etc., fillers include lactose, saccharose, mannitol, etc., compaction agents include microcrystalline cellulose and calcium monoacid phosphate, lubricants include stearic acid, polyethylene glycol, magnesium stearate, talc, silicon dioxide, etc., disintegration aiding agents include potato starch, sodium carboxymethylcellulose, etc., wetting agents include sodium lauryl sulfate, etc. The tablets are prepared in accordance with conventional ways.

Other formulations include liquid formulations, such as oil formulations, syrups, elixirs, emulsions, suspensions, etc., for topical use, or the drug formulation can be provided as a powder for dispersion in a non-aqueous or other suitable liquid carrier medium. Additives to the liquid medium for suspensions include sorbitol, cellulose derivatives, glucose, gelatin, aluminum stearate, hydrogenated edible fats, etc.; emulsifiers lecithin, gum arable, sorbitan monooleate, etc; other additives include ethanol, oil of almond, fatty esters, fractionated plant oils. For antioxidants and stabilizers, one may use methyl or propyl paraben, sorbic acid, etc. Other additives include coloring agents, fragrances, sweeteners, etc.

Alternatively, one may formulate the subject compositions as suppositories, inhalants, topical formulations, intramuscular or intravascular injection solutions or suspensions, etc., in accordance with conventional ways, or the like.

Other preparations include lipids. For example, boswellic acids can be extracted from resin using nonpolar solvents or lipids. Such preparations in lipids do not interfere with the modification synthesis and can be applied prior or after modification. Such compositions can be useful for administration across cellular membranes. In particular, preparations comprising lipids can be useful for delivery across the skin. In such situations, salves, creams, and ointments can be used.

In other situations, it can be desirable to regulate the absorption of the modified compounds and/or other phytochemicals by the tissue to be treated. Encapsulation of compositions in liposomes or use of slow-release formulations can provide more stable delivery of the desired agents. Many such systems are known to those of skill in the art.

The dosage of a modified boswellic acid composition described by example herein can generally be in the range of about 0.001 to about 1 mg/kg tor internal use, about 1 to about 100 mg/kg tor external use. Generally for internal use, a dose in the range of about 0.1 to 1 g is useful, and for external use usually about 1 to about 10 g per dose, depending upon the purpose of the therapy, the manner administered and the nature of the dose. In many instances, the subject compositions may be used with other compositions in a combination therapy to provide enhanced efficacy.

In situations in which slow release of the phytochemical is desired or degradation of the modified composition is anticipated, larger doses can be used, so that over time, the delivery of a desired therapeutic dose in a range described, above can be obtained.

The subject compositions have therapeutic effects in a number of indications, such as various neoplasias, systemic or local inflammatory diseases, of organs or organ systems or diseases having a substantial inflammatory component. Various regimens may be employed, giving daily doses of front about 1 to 14 administrations per week. By monitoring the response of the patient, one can determine the effective dosage, although studies in animals have shown that the subject compositions have very little adverse effect, when used appropriately.

The following examples are offered by way of illustration and not by way of limitation.

EXAMPLES

In the examples 1 to 5 below, extracts were made from commercially available *Boswellia* Frereana gum according to the methods described above. Organic extraction of the crude gum, transfer into an alkaline aqueous phase followed by re-acidification and back extraction into an organic phase yields only a slightly purified material, and compositions vising pure forms of boswellic acid are anticipated to yield more pure forms of polyol modified boswellic acid.

All of the synthesis that is detailed in the examples below are to be performed in a hermetically sealed glass reactor equipped with a stir rod and temperature controlled jacket. The bead space of the reactor is to be continuously Hushed with dry nitrogen unless otherwise specified.

Example 1: Preparation of a Polyester Diisocyanate

In this example a castor-derived hydroxyl-terminated ricinoleate derivative is used as the diol. One equivalent of polycin D-265 (212 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups. (2×42 Dalton) per product molecule by the total weight of the product molecule (424 Dalton+2×174 Dalton) yielding approximately 10.9%.

Alternatively, a lower molecular weight diol may be used, such as polycin D-290 where 1 equivalent of polycin D-290 is 193 g and the target % NCO is 84/(386+348)=11.4%.

Alternatively, a higher molecular weight diol may be used, such as polycin D-140 where 1 equivalent of polycin D-140 is 400 g and the target % NCO is 84/(800+348)=7.3%.

All polycin diols are available from Performance Materials (Greensboro, NC) and toluene diisocyanate is available from Sigma-Aldrich (Milwaukee, WI).

Example 2: Preparation of a Polyether Diisocyanate

In this example a polyether hydroxyl-terminated copolymer of 75% ethylene oxide and 35% propylene oxide is used as the diol. One equivalent of UCON 75-H-450 (490 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9 %. The target % NCO is reached when every hydroxyl group in the mixture is reacted with an NCO group. Ideally, the result is a single diol endcapped with two diisocyanates. This outcome can be enhanced by slow addition of the diol to the diisccyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (980 Dalton+2×174 Dalton) yielding approximately 6.3 %.

Polyether copolymers of ethylene oxide and propylene oxide diols are available from Dow Chemical (Midland, MI)

Example 3: Preparation of a Polyester Triisocyanate

In this example a castor-derived hydroxyl-terminated ricinoleate derivative is used as the triol. One equivalent of polycin T-400 (141 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=13.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (282 Dalton+2×174 Dalton) yielding approximately 13.3%.

The above reaction will yield a viscous product. A less viscous product can be obtained by adding propylene carbonate to the initial mixture. Additions up to 100% by weight of propylene carbonate are useful. Adjustment to the target NCO of the mixture must be performed using standard methods, or the propylene carbonate may be added after reaching the target % NCO.

Propylene carbonate is available from Sigma-Aldrich (Milwaukee, WI).

Example 4: Preparation of a Polyether Triisocyanate

In this example a polyether hydroxyl-terminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per 14 hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisccyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (3×42 Dalton) per product molecule by the total weight of the product molecule (9199 Dalton+3×174 Dalton) yielding approximately 1.3%.

Multranol 9199 is available from Bayer (Pittsburg, PA).

Example 5: Preparation of a Polyol Triisocyanate from Polyol Diol

Any of the diisocyanates prepared in Examples 1 and 2 and me trimerized by the addition of a low molecular weight triol such as polycin T-400 or trimethylolpropane (TMP). In this example TMP is used, but the method is adaptable to any triol. Complete trimerization of the diisocyanates of Example 1 and 2 will result in viscous products. To yield a lower viscosity product propylene carbonate can be employed or less triol can be used, in the later case, a mixture of diisccyanate and triisocyanate is obtained.

In this example the product of Example 2 is used as the polyether diisocyanate. One equivalent of Example 2 (682 g) is combined with 0.1 equivalent TMP (44.7 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=5.8%. The target % NCO is reached when every hydroxyl group in the mixture is reacted with an NCO group. The ideal % NCO is calculated by dividing the weight fraction of the functional isocyanate groups 10%(3×42 Dalton) and 90%(2×42) per product molecule by the total weight fraction of the product molecule (3×1364 Dalton+134 Dalton)+1364 yielding approximately 0.3 %+5.5%=5.8%.

TMP is available from Sigma-Aldrich (Milwaukee, WI).

Example 6: Preparation of a Modified *Boswellia* Extract Using the Triisocyanate of Example 4

The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

In this example the product of Example 4 is used as the polyether triisocyanate mixture. One hundred grams of Example 4 is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Example 7: Preparation of a Modified *Boswellia* Extract Using the Triisocyanate/Diisocyanate of Example 5

The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

In this example the product of Example 5 is used as the polyether diisocyanate/triisocyanate mixture. One hundred grams of Example 5 is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken, if % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added, to the mixture and the mixture is reacted so that % NCO=0 is obtained.

Example 8: Preparation of a Highly Branched Modified *Boswellia* Extract with Absorbable Links Diol and triol can be combined to form a multi-branch polymer. In this instance, the Multranol 9199 triol is chain extended with polycin D-265 diol. The diisocyanate form of Example 2 is useful in chain extending the triisocyanate form of Example 4. We wish to have on average 2 diisocyanates for every 3 triisocyanates, which forms a 5 armed isocyanate.

In this example 0.09 equivalents (292 g) of Example 4 is mixed with 0.04 equivalents (26.6 g) of Example 2. The triisocyanates of Example 4 and diisocyanates of Example 2 are chain extended with 0.08 equivalents lysine diamine to form a 5 armed isocyanate. One hundred grams of this reaction product is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Lysine diamine is available from Sigma-Aldrich (Milwaukee, WI).

Example 9: A Topical Therapeutic of Modified *Boswellia* Extract

Any of Examples 6-8 can be mixed with hydrogenation products of boswellic acid-containing vegetable extracts, boswellic acid, physiologically acceptable salts of boswellic acid, derivatives of boswellic acid, physiologically acceptable salts of these derivatives, boswellic acid-containing vegetable preparations or keto boswellic acid-containing vegetable extracts. Hydrogenation products of further ingredients of *Boswellia* extract, such as tirucallic acid or other triterpenoid compounds, salts or derivatives thereof and vegetable extracts containing these compounds, are also useful in a therapeutic topical.

Example 10: A Solid Ingestible of Modified *Boswellia* Extract

Medicine in the form of tablets or granules or pellets can be formed using conventional methods. The granules or pellets preferably are in the form of conventional capsules. Along with the active substance or the active substance extract the granules or tablets contain conventional pharmaceutically acceptable additives, such as binders, e.g. pregelatinised corn starch, polyvinyl pyrrolidone or hydroxypropylmethyl cellulose, fillers, such as lactose, saccharose, mannitol, corn starch, microcrystalline cellulose or calcium hydrogen phosphate, lubricants, such as stearic acid, polyethylene glycol, magnesium stearate, talcum or silicon dioxide, blasting agents, such as potato starch, sodium starch glycolate or sodium carboxymethyl cellulose and in particular the known superdisintegrating agents and optionally wetting agents, such as sodium lauryl sulfate. Tablets, pellets or capsules may be coated in known manner (e.g. with a water-soluble or an enteric coating) or they can be available without coating.

Example 11: A Liquid Ingestible of Modified *Boswellia* Extract

In this example the modified *Boswellia* extract is a liquid preparation tor oral administration. Liquid preparations for oral administration may be present as aqueous or oily solutions, syrups, elixiers, emulsions or suspensions, for example. Formulations can also be available as dry product for reconstitution with a suitable solvent. The production of such liquid preparations is also known and, where appropriate, conventional additives may be present, which include suspending agents, such as sorbitol, cellulose derivatives, glucose, sugar syrup, gelatin, aluminum stearate gel or hydrogenated cooking fats, emulsifiers, such as lecithin, gum Arabic or sorbitan monooleate, non-aqueous carriers, such as almond oil, oily esters, ethyl alcohol or fractionated vegetable oils, preservatives, such as methyl or propyl-parahydroxybenzoate or sorbic acid, buffers, gustatory substances and flavoring agents, coloring substances and sweetening agents.

Example 12: An Injectable of Modified *Boswellia* Extract

Preparations for injections include those for the intravenous, intramuscular, subcutaneous, intrathecal or intracranial injection, which are suitably available in unit dose form, such as ampoules, or in multiple-dose containers. The formulations optionally contain a conventional preservative and further conventional auxiliary substances. The injectables according to the invention can also be prepared as suspensions, solutions or emulsions in oily or aqueous carriers in a manner known to the person skilled in the art. For example, the preparations may be available as suspensions, solutions or emulsions in oily or aqueous carriers and contain conventional auxiliary substances, such as suspending, stabilizing and/or dispersing agents and/or agents for adjusting the tonicity. Here, the agent can also be present as a dry powder for reconstitution in a suitable carrier.

These examples are not meant to be limiting to the present invention.

Reference will now be made to the exemplary embodiments of devices illustrated in the drawings, and specific language will be used herein to describe the same. It will nevertheless be understood that no limitation of the scope of the invention is thereby intended. In particular, there are numerous compositions known in the art for providing implantable nonspecific therapeutic delivery, including microsphere encapsulation and dispersion within a polymeric carrier, multi-layer architectures, mechanically fenestrated polymeric sheets, and the like. Further, these examples do not limit alterations and further modifications of the inventive features illustrated herein, and additional applications of the principles of the inventions as illustrated herein, which would occur to one skilled in the relevant art and having possession of this disclosure, are to be considered within the scope of the invention.

The present invention makes use of biodegradable materials that will be gradually dissolved in the body of a living subject, and which can be impregnated with a triterpene composition, thereby resulting in the gradual release of triterpenes into the surrounding tissue of the subject's body. Suitable biodegradable materials will gradually disassociate in vivo, and will not have any substantial toxic or other harmful effect on the subject. Examples of suitable biodegradable materials are polylactic acid, polyglycolic acid, dilactic acid, and lactic acid-glycolic acid copolymers. Polyglycolic acids having molecular weights between 1000 and 50,000 daltons are preferred. Dilactic acid/polyglycolic acid ratios of 75/25 and 85/15 by weight are commercially available and are useful in the present invention. Such biodegradable materials can be purchased from Sigma Aldrich, Milwaukee. WI Additional suitable materials are those with good mechanical properties which have been modified to breakdown in the body. For instance, copolymers of those materials mentioned previously and polyurethanes, or polyurethanes synthesized with diisocyanate with a degradable link between the isocyanate groups.

Variations in the composition of the polymer carrier, such as the thickness, molecular weight, crosslink density, hydrophilicity of each of the biodegradable materials and their relative proportions, affect the release rate and release duration of the triterpenes, and therefore allow the rate and duration to be modified to meet the requirements of different treatment situations. In general, the lower the molecular weight of the biodegradable material, the faster it will disassociate and release the triterpenes. Suitable carrier architectures in this regard include multiple layers of degradable polymers with varying rates of disassociation. Variation in disassociation rate can be achieved simply by varying the ratio constituents of a copolymer, for example the number ratio of dilactic acid and polyglycolic acid. Devices comprised of layers of polymers with different release rates may employ a first high release rate layer which releases triterpenesperi-operatively and a second layer may be designed to provide a steady flux of triterpenes for an extended period of time.

The polymer carrier of the present implant may be insoluble in the triterpene, if the triterpene composition is prepared as a solution. Preferably the polymer carrier is also water-insoluble. The polymer matrix should be stable during storage, during sterilization, and should not degrade in the body significantly over a period of at least 2 days, preferably at least 2 weeks tor instance a month or more. The polymer carrier may be substantially non-crosslinked, such as formed from linear polymeric chains which may additionally include surface-bonding groups for stable surface binding to an implant. Optimum stability is achieved when the polymer carrier is covalently crosslinked and/or covalently bound to the implant surface.

A crosslinked polymer carrier sheet may be created by polymerisation of monomers including a crosslinking monomer which form crosslinks during the polymerisation reaction. Where the polymerisation is a condensation process, 3-functional and higher-functional monomers can be used to achieve branching and crosslinking.

Alternatively, the polymeric units of the polymer carrier are not crosslinked, but rather of suitable length or geometry to result in entanglement when cooled or a solvent is driven off. This approach has several manufacturing advantages, since sheets can be easily constructed by heat extrusion or casting of the polymer suspended in an organic solvent. For optimum stability and manufacturing of the polymer carrier, it is preferred the precursor polymer solution be crosslinkable by the application of heat or light energy. Such preferred precursors may additionally be solid and dissolvable in a solvent, so that a sheet may be formed by solution casting and then subsequently stabilized by the application of energy and the initiation of polymerization.

In another exemplary embodiment, the present triterpene releasing medical device includes a final absorbable coating. The final coating is applied over the drug releasing polymer, and the final coating acts as a barrier to allow for the controllable release of the triterpene compound from the surface of the medical implant. According to one exemplary embodiment, the final coating may be composed of ethylene vinyl acetate copolymers.

In another exemplary embodiment, the final coating may be composed of copolymers of ethylene and alkyl acrylate or polyalkylmethacrylate.

In yet another exemplary embodiment, the final coating may be composed of absorbable polyurethanes, comprised of copolymers of ethylene and propylene oxides linked by urethane bonds comprised of degradable links. As those skilled in the art will appreciate, all the various layers of the device should possess similar swell characteristics when placed in the body so that delamination or distortion of the implant does not substantially occur. For implants where flexibility is not a requirement stiff final coatings may be applied, for example polycaprolactone.

In another aspect, additional embodiments are directed to medical devices having a triterpene releasing component and a final coating that is hydrophilic. Hydrophilic surfaces are less inflammatory, resist protein deposition, and are less likely to form adhesions.

The triterpene releasing medical devices of the present invention include more than planar implants, for example balloons, expandable stents and self-expanding stems, stent grafts, vascular grafts, heart valves, heart valve sewing rings, annuloplasty rings, venous valves, sutures, sutureless coronary anastomosis devices connectors, implantable catheters and shunts, and other access devices. In many instances a single coating of polymer carrier loaded with triterpene compound is sufficient, and preferably is covalently bonded to the bulk composition of the de vice. Alternatively, the triterpene compositions disclosed herein cart also be incorporated into the bulk materials from which the pros theses are constructed. In these instances, the triterpene compound is eluted rather than released by disassociation of a carrier polymer.

In another aspect, the present invention provides a method of manufacturing an adhesion-inhibited medical tissue support mesh or surgical barrier material. This method includes providing a tissue support mesh material, and incorporating on the material an effective amount of: a triterpene compound with specific anti-inflammatory properties to inhibit the formation of tissue adhesions.

In general, triterpenes are hydrophobic, and can be made less so by addition of polyether chains, in particular polyethylene oxide. Variations in hydrophilicity can be achieved by grafting onto the triterpenes polyether chains comprising varying ratios of polyethylene oxide and polypropylene oxide. The greater the proportion of propylene oxide to ethylene oxide in a copolymeric polyether is, the more hydrophobic the final composition of polyether chain and triterpene.

FIG. 1 illustrates how a structure 100 comprising a hydrophobic triterpene end 102 and a hydrophilic polyether end 104 orient relative to a hydrophilic base layer 106. The hydrophilic end 104 naturally associates with the hydrophilic base layer 106, thus creating a concentration of therapeutic triterpene 102 closest to the tissue contacting surface 108. The benefit to this configuration is that the beneficial anti-microbial aspect of triterpenes is immediately present on the surface of the implant without requiring release. The polyether aspect 104 of the modified triterpene 100 aids in the passage of the modified triterpene 100 into surrounding body tissue, since modified triterpene 100 is relatively more hydrophilic than an unmodified triterpene.

Thus once released, the modified triterpene act to reduce or eliminate inflammation and a foreign body response. Triterpenes are also recognized to aid in healing, and in some instances promote angiogenesis, which is a critical aspect of healthy, stable tissue remodeling. It has been recognized that regenerated tissue devoid of cells is inherently unstable and undergoes a continuous process of remodeling, which is associated with pain. An implant that promotes angiogenesis, and hence blood flow, will result in repair tissue which is rich in cells and far less likely to remodel.

Figure 2:
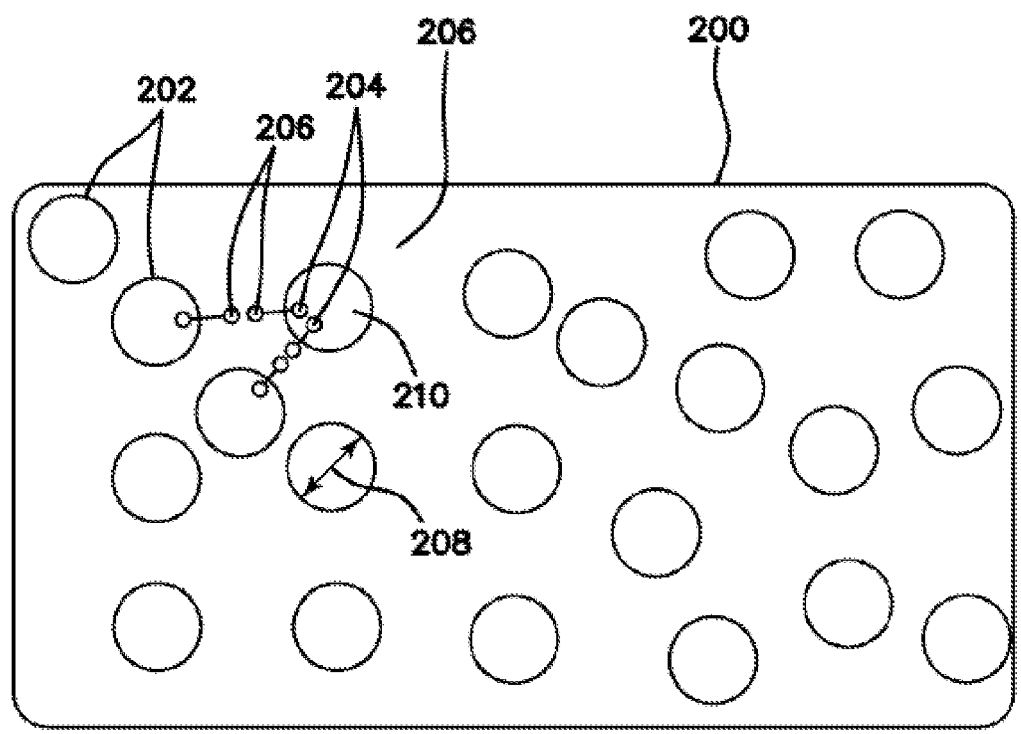
FIG. 2 schematically illustrates triterpene release from a tissue implant containing miscelles when biodegrading at a tissue repair site.

FIG. 2 illustrates a micelles structure to a triterpene releasing implant 200. Micelles 202 form in solutions where there is a difference in polarity between various constituents. In the solid example 200, the micelles 202 are frozen in place by the evaporation of solvent from a solution containing polymer carrier and triterpenes. The micelles structure 202 can be greatly altered by adjusting the hydrophilicity of the triterpene fraction 204 relative to the hydrophilicity of the polymeric carrier fraction 206. Generally, the greater the difference in hydrophilicity the larger the diameter 208 of the micelles structure. It can readily be seen that as the polymer carrier 206 disassociates, the polymer carrier 206 acts as a shell around the triterpene fraction 204 regulating elution rate. In some instances the polymeric carrier blocks elution entirely, and thus the triterpene 204 is released only when the micelle is opened 210 by disassociation of the polymer carrier 206.

Figure 3:
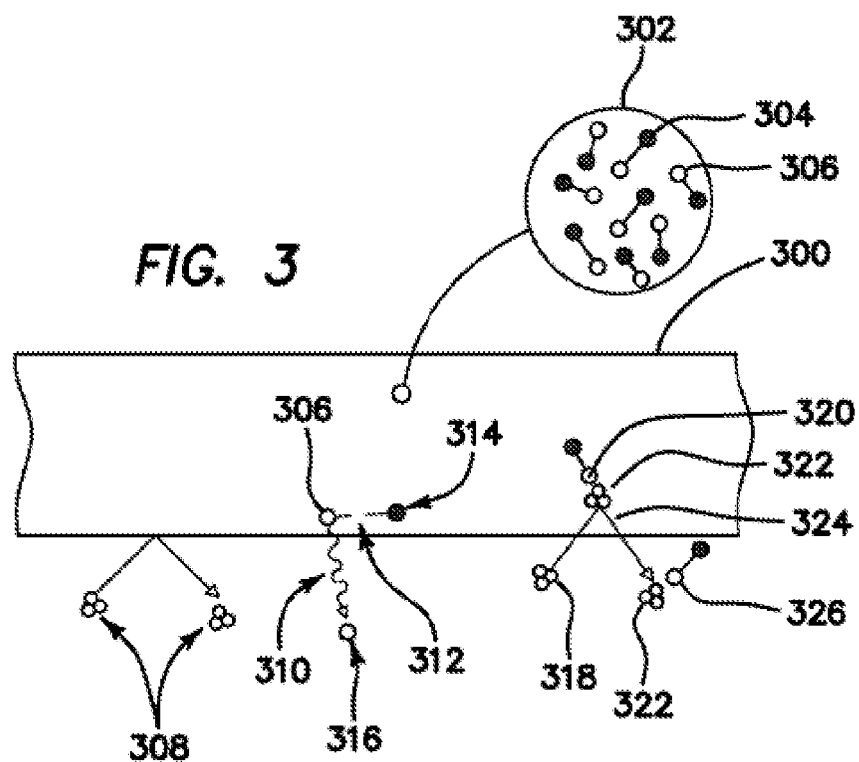
FIG. 3 schematically illustrates triterpene release from a tissue implant wherein the triterpene is homogenously dispersed within a carrier polymeric matrix when biodegrading at a tissue repair site.

FIG. 3 illustrates a triterpene implant 300 where the triterpene fraction is homogenously distributed. The magnified out take 302 shows polymer carrier molecules 304 and triterpene molecules 306 homogenously distributed at the scale of molecular dimensions. When the polymer carrier molecules 304 are hydrophobic water 308 does not penetrate the volume of the implant 300. In this case, release of triterpene molecule 310 occurs when polymer carrier molecules are hydrolyzed 312 where smaller polymer carrier pieces 314 can now be solubilized and triterpene molecule 316 is released. When the polymer molecules 304 are hydrophilic water 318 penetrates the volume of the implant 300. In this case, triterpene molecule 320 associates with water molecule 322 and diffuses 324 through implant bulk 300 and triterpene molecule 326 is released. Clearly, this diffusion mechanism is also applicable to the micelles structure illustrated in FIG. 2 when these hydrophilic conditions are met.

Figure 4:
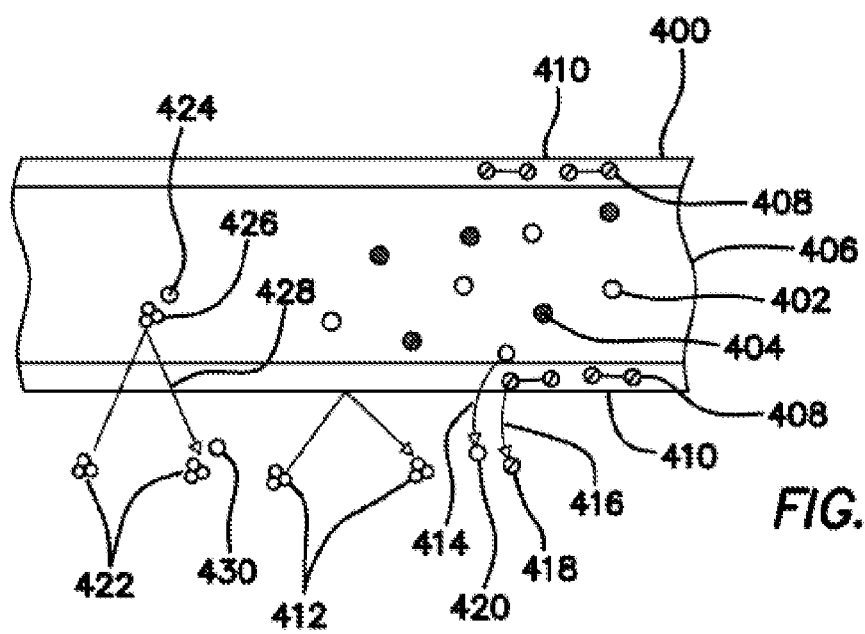
FIG. 4 schematically illustrates triterpene release from a tissue implant wherein the triterpene is sandwiched between layers of a carrier polymeric matrix when biodegrading at a tissue repair site.

FIG. 4 illustrates a triterpene implant 400 where the triterpene fraction 402 is homogenously distributed in first polymer carrier 404 comprising triterpene reservoir layer 406. Triterpene reservoir layer 406 is sandwiched between second polymer carrier 408 comprising final layers 410. Preferably triterpene reservoir layer 406 is comprised of hydrophilic polymer carrier 404. When final layers 410 are hydrophobic water 412 does not penetrate the volume of the implant 400. In this case, release of triterpene molecule 414 occurs when second polymer carrier molecules are hydrolyzed 416 where smaller second polymer carrier pieces 418 can now be solubilized and triterpene molecule 420 is released. When final layers 410 are hydrophilic water 422 penetrates the volume of the implant 400. In this case, triterpene molecule 424 associates with water molecule 426 and diffuses 428 through implant bulk 400 and triterpene molecule 430 is released.

Hydrophobic biodegradable polymer carrier molecules of the present invention can be a member selected from the group consisting of polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly (amino acid)s and polycarbonates.

Alternatively the hydrophobic biodegradable polymer carrier molecules of the present invention can be a member selected from the group consisting of random block copolymers of the above and a polyether, where the polyether is polymerized directly to the above or polymerized through a urethane or urea link, or the polyether itself may be a macropolymer of polyurethane/polyurea(urethane).

The random block copolymer described above can be synthesized by polymerizing lactone type heterocyclic esters and polyether glycols at a temperature of 80 to 130° C. using stannous octoate (Sigma Aldrich, Milwaukee, WI) as a catalyst. For example, they may be prepared via ring opening bulk polymerization of one of the cyclic ester monomers, such as lactide, glycolide, or 1,4-dioxan-2-one with poly (ethylene glycol) or poly(propylene glycol) in the presence of stannous octoate as a catalyst at 80° C. to about 130° C. When the 1,4-dioxan-2-one is used as the monomer, the preferable reaction temperature is 80° C. to about 110° C. When a copolymer of 1,4-dioxan-2-one and lactide is used, the 1,4-dioxan-2-one monomer is first reacted with poly (ethylene glycol) or poly(propylene glycol) at 100° C. to about 130° C., the lactide monomer is then slowly added to increase the degree of polymerization of 1,4-dioxan-2-one. In creating these random block copolymers it is preferred the lactone type monomers be uniformly distributed amongst the polyether monomers.

Accordingly, these monomers preferably are of low molecular weight, between 100 and 2000 Dalton. The synthesis is carried out in steps intended to chain extend the copolymer with alternating lactone type and polyether blocks. To facilitate this stepwise addition the reaction may preferably be carried out in an organic solvent. The block copolymer product is dissolved in dichloromethane or acetone, precipitated in diethyl ether, hexane, pentane, or heptane, followed by drying.

The copolymers as described above will consist of alternating hydrophobic and hydrophilic blocks. Those copolymer carrier molecules will act as a spacing architecture to which the triterpene molecules will be associated when the triterpene fraction and carrier molecule fraction are solubilized in an organic solvent.

Figure 5:
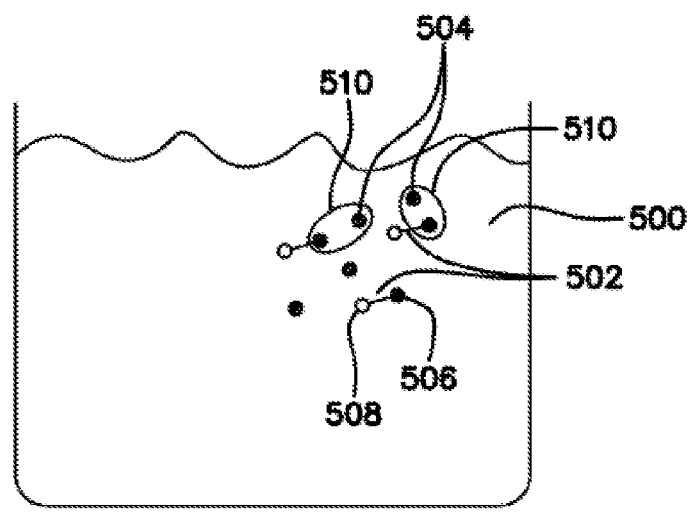
FIG. 5 schematically illustrates a liquid composition of copolymer molecules and triterpene molecules. In this illustrated case, the triterpene molecules are modified with a hydrophobic polyether comprised of triterpene group and polyepropylene group.

FIG. 5 illustrates a liquid composition 500 of copolymer molecules 502 and triterpene molecules 504. In this illustrated case, the triterpene molecules 502 are not modified and hydrophobic. The copolymer molecule 502 is comprised of hydrophobic block 506 and hydrophilic block 508. The hydrophobic triterpene 502 associated with the hydrophobic blocks 506 of copolymer molecule 502 as illustrated in 510.

Figure 6:
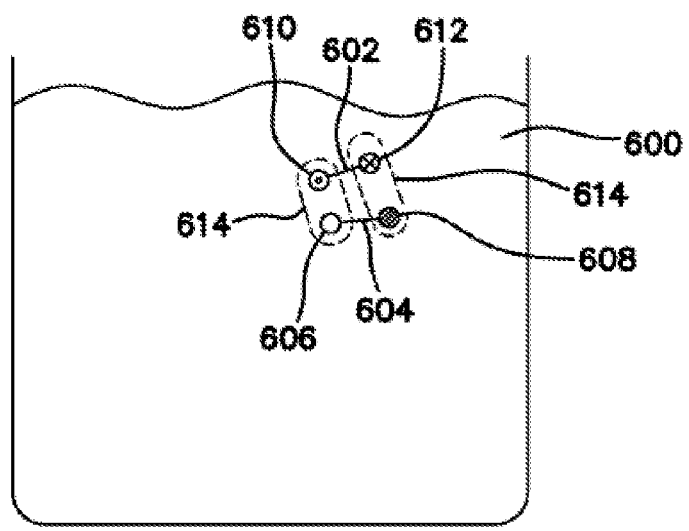
FIG. 6 schematically illustrates a liquid composition of copolymer molecules and triterpene molecules. In this illustrated case, the triterpene molecules are modified with a hydrophilic polyether comprised of triterpene group and polyether group.

FIG. 6 illustrates a liquid composition 600 of copolymer molecules 602 and triterpene molecules 604. In this illustrated case, the triterpene molecules 602 are modified with a hydrophilic polyether comprised of triterpene group 606 and polyether group 608. The copolymer molecule 602 is comprised of hydrophobic block 610 and hydrophilic block 612. The triterpene group 606 of the modified triterpene molecule 604 associates with the hydrophobic blocks 610 of copolymer molecule 602 and the polyether group 608 of the modified triterpene molecule 604 associates with the hydrophilic blocks 612 of copolymer 602 as illustrated in 614.

Alternatively, the association of polymer carrier molecules and triterpene molecules can be accomplished without solvent when the melting points of polymer carrier molecules and triterpene molecules is lower than the temperature that results in disassociation of either the polymer carrier molecules or triterpene molecules. Preferably, the copolymer and triterpene molecules have melting temperatures of below about 80° C. and above 40° C. It is desirable that the combination of copolymer carrier and triterpene be in solid phase at body temperature.

As illustrated in FIGS. 5 and 6, the biodegradable implant of the present invention comprised of carrier polymer and triterpene compound forms networks of carrier molecules and triterpene molecules which control the rate of release of the triterpene and polymeric fractions. The biodegradable implant employed in the present invention should be biocompatible, be degradable into products harmless to the human body after a given time in vivo, and be uniformly disassociated at a slow rate when implanted in the body. The degradation may be a combination of solvation, diffusion within the bulk volume of the implant, hydrolysis, enzymatic lysis, and mechanical disassociation.

When introduced into the body, the composition of the present invention acts as a triterpene release device in addition to other functional aspects, for example, acting as a tissue adhesion barrier, tissue defect repair device, etc. The poorly water-soluble triterpenes are entrapped within a degradable or eluting polymeric architecture. Therefore, the triterpene or modified triterpene distributed in micelles or bulk polymer structure are slowly released from the implant thereby providing a constant triterpene circulation concentration for an extended period of time. Thus the compositions of the present invention are especially useful for the sustained delivery of poorly water soluble triterpenes having solubilities of less than 1 mg/mL at ambient temperatures.

Alternatively, the described implant structure can be employed to release at a constant rate modified triterpenes which have been so modified to have a higher solubility. Additionally, the triterpenes can be modified in a way which groups multiple triterpenes on a multi-armed polyether.

Examples of these triterpenes and modified triterpenes include anticancer agents, anti-inflammatory agents, antifungal agents, anti-emetics, and anti-hypertensive agents. It is recognized that the implants of the present invention can serve as generic drug release devices wherein the drug to be released is of approximately the same hydrophobicity as the triterpene groups. Thus the triterpene traction can be augmented by other drugs, examples of these are: anticancer agents such as paclitaxel, docetaxel, camptothecin, doxorubicin, daunomycin, cisplatin, 5-fluorouracil, mitomycin, methotrexate, and etoposide; anti-inflammatory agents such as indomethacin, ibuprofen, ketoprofen, flubiprofen, dichiofenac, piroxicam, tenoxicam, naproxen, aspirin, and acetaminophen; antifungal agents such as itraconazole, ketoconazole and amphotericin; sex hormones such as testosterone, estrogen, progesterone, and estradiol; steroids such as dexamethasone, prednisolone, betamethasone, triamcinolone acetonide and hydrocortisone; antihypertensive agents such as captopril, rantipril, terazosin, minoxidil, and parazosin; antiemetics such as ondansetron and granisetron; antibiotics such as metronidazole, and fusidic acid; cyclosporines; prostaglandins; and biphenyl dimethyl dicarboxylic acid.

Release accelerators may be used in the implant of the present invention. Physiologically inert, water soluble polymers may be incorporated in the polymer carrier, e.g. low molecular weight methyl cellulose or hydroxypropyl methyl cellulose (PMC); sugars, e.g. monosaccharides such as fructose and glucose, disaccharides such as lactose, sucrose, or polysaccharides such us cellulose, amylase, dextran, etc. Alternatively, the accelerator may be a physiologically active agent, allowing for a combined therapeutic formulation. The choice of accelerator in such a case will be determined by the desired combination of therapeutic activities.

Alternatively release retardants may be used in the implant of the present invention. Agents of interest as release retardants include non-water soluble polymers, e.g. high molecular weight methylcellulose and ethylcellulose, etc., low water soluble organic compounds, and pharmaceutically active hydrophobic agents.

Normally the implant will be formulated to release the active agent(s) over a period of at least about 7 days, more usually at least about one month, and usually not more than about one year. Seven days is important in the application of an implant intended to reduce adhesion formation, since post-surgical adhesions are known to develop within 7 days. The therapeutically active agent is released within a therapeutic dosage which does not vary by more than about 30% for a period of at least about 7 days. For the most part, the bulk of the implant will have a physiological lifetime at the site of implantation at least equal to the desired period of administration, preferably at least twice the desired period of administration, and may have lifetimes of 5 to 10 times the desired period of administration. The desired period of release will vary with the condition that is being treated. For example, implants designed for hernia repair may comprise an anti-microbial triterpene with a release period of from about 3 months to 1 year; 2 weeks; while implantation of a soft tissue repair mesh in a site where a repair was previous performed and has subsequently become infected may require a release period from about 1 year to 3 years.

Other structures that modify release rate concern implants comprised of one or more layers of the same or different composition, where the layers may be cross-linked, of different molecular weight, different density or porosity, or the like. For example, for a surgical barrier application the center layer would comprise a polylactate mixed with triterpene compound and this layer would be coated with a polylactate polyglycolate copolymer also combined with triterpene compound, so as to create two rates of triterpene release. Most ratios of lactate to glycolate employed will be in the range of about 1:0.1 to 1:1. Alternatively, the center could be polyvinyl alcohol coated with polylactate, so that on degradation of the polylactate the center would dissolve and be rapidly washed out of the implantation site.

The purpose of this construct would be to mitigate against mechanical fracturing of the implant and the subsequent formation of hard fibrous centers nucleated with implant fragments. The operational idea here is that when the implant reaches a minimum tensile strength during the process of degradation, the implant dissolves into molecular sized constituents rather than macroscopic fragments.

Other structures that modify release rate concern implants comprised of pores. Coating and bulk polymer carrier formulations capable of forming pores when a solid implant is formed may be loaded with the triterpene compound during pore formation or after pore formation. Some liquid compositions inclined to form pores when solidified and when mixed with the triterpene compound while in a liquid state, will tend to segregate the triterpene compound into the pores when the hydrophilicity of the polymer carrier is sufficiently different from the hydrophilicity of the triterpene compound. Alternatively, porosity in a bulk solid carrier polymer can be achieved post solidification by employing a water soluble agent which is later dissolved out of the formed solid polymer. Pore forming agents may be liquid or solid, such as polyethylene glycol or micro-granulated sugar, mixed with water insoluble polymers.

Other water soluble pore forming agents include, for example, polypropylene glycol, various sugars (lactose, sucrose, dextrose, etc.), salt, poloxamers, polyvinyl alcohol and other water soluble food grade and other excipients. When PEG is used as a pore forming agent of the invention, the molecular weight of PEG is in the range from about 200 to about 20,000, preferably from about 1,000 Dalton to about 10,000 Dalton. Most preferably, PEG having a molecular weight of about 8,000 Dalton is used.

The pore forming agent is used in the formulation of the invention in the amount effective to regulate the release of a biologically active compound at a desired rate. Preferably, the effective amount of the pore forming agent provides long term delivery of the active agent thus increasing the useful life of a sustained-release triterpene implant. The effective amount of the pore forming agent will depend on the desired rate and duration of the release and the ability to form a continuous microporous film during the casting process.

Additional methods of creating porosity in the bulk carrier polymer are polymerization reactions which result in release of a reaction byproduct in the gas phase. These polymerization reactions may be chain extensions or crosslinks, and combinations. Polymerisation which is a condensation process, 3-functional and higher-functional monomers can be used to achieve branching and crosslinking.

Useful polymerizations, for example, are urea formation between isocyanate endcapped polyethers when the polymer solution prior to solidification contains a small amount of water. Alternatively the polymer solution may comprise a mixture of slow reacting polyether isocyanates and polyether amines.

Preferable reaction rates that form and retain porosity when formed in polymer solutions containing polyether isocyanates and water are between 1 minute and 1 hour, more preferably between 3 minutes and 10 minutes. Suitable isocyanate groups are generally aromatic isocyanates, and preferably a low molecular weight diisocyanate, for example toluene diisocyanate. These isocyanates can be employed in the synthesis of polyether isocyanates by formation of urethane links between the hydroxyl groups on the poly ether and isocyanate groups of the diisocyanate. Preferable reaction rates that form and retain porosity when formed in polymer solutions containing polyether isocyanates and polyether amines are between 1 minute and 1 hour, more preferably between 3 minutes and 10 minutes.

Suitable isocyanate and amine groups are generally aliphatic isocyanates and amines, and preferably a low molecular weight diisocyanate, for example isophorone diisocyanate and isophoronediamine. These isocyanates can be employed in the synthesis of polyether isocyanates by formation of urethane links between the hydroxyl groups on the polyether and isocyanate groups of the diisocyanate. These amines can be used directly without attachment to a polyether. It should be understood that solidification of the liquid polymer solution occurs by urea formation between polyether isocyanates and amines as well as urea formation between polyether isocyanates in the presence of water.

In the method of forming pores in the solidified carrier polymer the triterpene release half life varies with the square of the thickness of the solidified carrier polymer. In the present invention, in the application of a surgical barrier, thickness of implant is in the range 100 microns to 5 millimeters, most preferably in the range 200 microns to 500 microns. Release architectures employing pores may generally release the triterpenes too rapidly, especially when the triterpenes are modified to be more hydrophilic. Modification of the triterpene to suit a desired release rate may not be optimal for efficacy once the triterpene is released into the body. Decoupling the release rate from the hydrophobic character of the triterpene is generally desirable. The release half-life, and consequently period over which the triterpenes will be released, may be controlled by selection of a suitable coating thickness. The diffusion coefficient can be calculated by experiment.

The non-triterpene coating may be any biocompatible polymer which has been used to provide biocompatible coatings on stents or other implants. Preferably the polymer is biostable and hence water-insoluble, but also biodegradable or bioerodable. The polymer coating may be a hydrogel loosely adhered to the triterpene containing polymer carrier, such that the polymer carrier is the primary structure element. The diffusion of therapeutic molecules through hydrogels is well-studied, controllable and in particular provide controlled release delivery capability. The coating may be a polymer, for instance, a silicone hydrogel, a polyurethane, or polyethers, such as polyethylene glycol, polyamides, polyesters, such as hydroxy-butyric acid polymers and copolymers, poly(lactides) or polyacrylic polymers. Preferably the coating is a crosslinked hydrogel, since to be a good diffusing medium the molecular structure is preferably sufficiently open to provide conductance of the triterpenes, and without crosslinking would likely dissolve rapidly into the body.

In other application where a long half life is desired, the coating need not be a hydrogel. Useful polymeric coatings include ethylene vinyl acetate copolymers, copolymers of ethylene and alkyl acrylate or polyalkylmethacrylate, copolymers of ethylene and propylene, styrene butadiene rubber, or silicone based polymers. These polymer coatings are useful in applications where the triterpene delivery device is applied to an expandable or flexible medical device, for example, a balloon.

In the manufacture of these various release architecture solvents are typically utilized. In order to be stable in an implant environment the carrier polymer is broadly speaking hydrophobic, these substances are soluble in organic solvents such as, but not limited to, halogenated hydrocarbons, aromatic and aliphatic hydrocarbons, alcohols, cyclic ethers, ketones, such as methylene chloride, ethanol, tetrahydrofuran, toluene, acetone and 1,1,2 trichloroethane.

When the hydrophobicity of the solvent is similar to that of the triterpene compounds to be incorporated, the uniformity of the triterpene compound in the polymer carrier is greatly enhanced. The enhanced compatibility between the triterpene fraction and the carrier fraction results in a smoother surface when the solvent-polymer-triterpene solution is solidified by driving off the solvent. Furthermore, also closely matching the hydrophobicity between the polymer carrier and triterpene compounds provides a reproducible and predictable release rate upon exposure of the implant to a physiological environment.

It is generally easier to modify the hydrophobicity of the polymer carrier than modification of the hydrophobicity of the triterpenes. Modification of the hydrophobicity of the polymer carrier can be accomplished by adding conditioning polymer. Useful conditioning polymers include biostable polymers which are also biocompatible such as, but not limited to, polyurethanes, silicones, ethylene-vinyl acetate copolymer, polyethers such as homopolymers or copolymers of alkylene oxide, homo- or copolymers of acrylic, polyamides, polyolefins, polyesters, polydienes, cellulose and related polymers.

Bioabsorbable polymers that could be used include poly (L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-cotrimethylene carbonate), polyphosphoester, polyphosphoester urethane, poly(amino acids), cyanoacrylates, poly(trimethylene carbonate), poly(iminocarbonate), copoly (ether-esters), polyalkylene oxalates, polyphosphazenes and biomolecules such as fibrin, fibrinogen, cellulose, starch, collagen and hyaluronic acid. These and other polymer systems can be used if they can be dissolved or dispersed in a solvent system hosting the primary polymeric carrier.

In considering the delivery characteristics of copolymers factors that affect delivery rate include molecular weight, molecular morphology, crosslink density and fractional content of the initial monomer. The presence of monomers which did not participate in the copolymerization synthesis is art important drawback if optimization of delivery characteristics is required. The reactivity of glycolide, lactide and caprolactone towards ring-opening are very different, so copolymers of these monomers usually contain residual content of these monomers. The high temperatures that are usually required for complete monomer conversion makes it difficult to obtain a controlled monomer distribution in this type of copolymers, especially if the goal is to obtain a uniform distribution of monomeric units. Even more difficult are randomly polymerized terpolymers of these monomers.

Thus, there is a need, from a product standardization point of view, for a polymer carrier which is not synthesized by a process depending on ring-opening. In this respect absorbable polyurethanes and absorbable polyurca(urethanes) provide important advantages with respect to product uniformity.

In particular, absorbable polyurethanes can be synthesized by grafting a single glycolide, lactideorcaprolactone in between two isocyanate groups. More particularly, single isocyanate groups are attached to aromatic or aliphatic rings and these mono-isocyanates are bridged by glycolide, lactide, caprolactoneor low molecular weight co- or ter-polymers of these. Then a polyurethane can be synthesized by reacting polyethers with these degradable diisocyanates without the presence of monomers. The polyethers can be copolymers of ethylene oxide and propylene oxide without the presence of monomeric contaminants. Thus, the copolymer aspect useful in obtaining a desired hydrophobicity of the polymer carrier is decoupled from the degradable aspect of the carrier polymer.

It is important to recognize that polyether units can also be used to modify triterpene groups, thus different polyether segments can be associated with different physico-chemical properties. This natural compatibility between triterpenes modified with polyethers and a carrier polymer comprised of polyethers can be used to build into the implant high swelling degree, increased permeability, or slow degradation rate. Moreover, the degradation products of the carrier polymer (essentially polyethers) may be designed to work synergistically with the modified triterpenes to increase their therapeutic efficacy. For example, the triterpenes can be made more hydrophilic by polyether addition which then allows them to elute from the carrier polymer prior to significant degradation of the carrier polymer leading to a certain extent of phase separation, resulting in biphasic release patterns. In this respect, the carrier polymer acts as a moderator of the elution rate, where in the first instance modified triterpenes are released alone by elution and in the second instance modified triterpenes are released in association with polyether segments resulting from degradation of the carrier polymer.

As mentioned previously, it is preferred that when a copolymer is used as a carrier polymer wherein the comprising blocks A and B are significantly different in hydrophilicity, which is typically the case when the proportion of the blocks A and B is chosen to achieve a desired overall hydrophilicity, it is desirable to distribute the blocks A and B as uniformly as possible, most preferably repeating sequences of AB. This is desirable, as mentioned, to avoid macroscopic implant fragmentation of units that are strongly hydrophobic.

Where a high proportion of hydrophobic blocks are required to obtain the desired overall hydrophilicity, then the relatively hydrophobic blocks, for example BBBBBB may be pre-synthesized with a degradable block C, such as an ester. Accordingly, prior to copolymerization of A and B blocks, B blocks can be synthesized with an ester block, such as BBBCBBB. The hydrolysable polyester block can also be used in designing the degradation rate of the carrier polymer.

Incorporation of an amorphous ester block, essentially obtaining a terpolymer of blocks A, B and C provides more versatility in the design of the carrier polymer. For example, the overall hydrophilicity of a polymer comprised of ABA-BAB is different from a polymer comprised of AAABBB, although the number of each constituent block is the same. Use of the ester block C allows one to design a carrier polymer with relatively concentrated regions of A and B blocks without compromising the macroscopic degradation aspects of the carrier polymer. In summary, properties such as flex modulus, permeability, swelling characteristics, degradation behaviour and triterpene release characteristics can be tuned in a much better way using ester blocks to enable variation of block length as well as block ratio of hydrophobic and hydrophilic blocks.

It is important to utilize the ester block C in pre-synthesis copolymer procedures and consume the ester block entirely in the synthesis of a multi-unit block, for example, in the synthesis of AACAA. Alternating copolymer structures, such as ABAB requires that they must be prepared at relatively high temperatures (>100° C.) under inert conditions. Thus, when synthesizing the copolymer from blocks of A and B, the ester blocks must already be incorporated into one of the block structures. The reason for this precaution is that the higher temperatures required for ABAB synthesis Vs AAAA synthesis risk trans-esterification if free ester groups are present in the reaction.

The multi-block copolymers of the present invention do not suffer from this disadvantage since they can be prepared by incorporating the ester block within a previously synthesized block structure at rather low temperatures (>80° C.). This will avoid trans-esterification and other side-reactions, which may cause the generation of undesired degradation and other by-products. Also, advantageously the monomer sequence length of the copolymer is determined by the choice of building components and not so much by reaction time and temperature. An advantage of using multi-blocks incorporating ester units in the synthesis of copolymers of this invention over the known alternating multi-block copolymers is that they can be prepared by linking of multi-blocks using a multifunctional chain-extender, thus obtaining a copolymer with multi-block segments randomly distributed in the copolymer in 3 dimensions. In accordance with the invention, multi-block copolymers wherein the multi-block segments are randomly distributed in the copolymer are preferred. All possible multi-block ratios and segment lengths can be used, thus offering a wider range of possibilities to tune the properties.

Parameters, winch may be used to modify the triterpene release properties include type and relative amounts of monomers in the blocks, type of initiator, molecular weight of the blocks, weight percentage of different blocks, overall molecular weight of the multi-block copolymer and functionality and concentration of chain-extender.

The materials of the present invention have thermal properties that allow processing of the material in melt form at relatively low temperatures, or in solvent systems thus avoiding trans-esterification and other side reactions that cause the generation of undesired degradation and other by-products. At the same time, the thermal properties are such that the materials can be used as a triterpene delivery implant.

Examples of Devices

Since the implant of the present invention comprises a biocompatible carrier polymer which is degradable after a given time into products that are harmless to the human body and is excreted from the body, the triterpene release rate can be controlled by adjusting the content of each carrier polymer component. The release of the triterpene compounds is sufficiently slow to provide a constant concentration of the triterpene at the implantation site as well as in the circulation for an extended period of time. Therefore, the composition of the present invention can provide for excellent pharmacological effects.

The adjustability of the triterpene release rate is illustrated in the Examples that follow. In these Examples, in some instances only an extremely small amount of the triterpene is released into an aqueous medium at 24 hours. In other Examples, the triterpene is completely released into the aqueous medium within 24 hours. By the Examples provided it is shown the present invention can control the release of the triterpene by adjusting the structure and content of each component.

While the following preparations and examples are provided for the purpose of illustrating certain aspects of the present invention, they are not to be construed as limiting the scope of the appended claims. The chemical used in these examples can be obtained from Sigma-Aldrich, Milwaukee, WI, unless otherwise stated.

Example D1: An Implant of the Present Invention with Micelles

A 20% solution of polylactic acid 704 (Beringer-Ingelheim) and acetone was prepared. Into 50 ml of the polylactic acid solution was mixed 1 ml of modified boswellic acid. The mixture was mixed in a beaker under gentle agitation until the mixture reached a viscosity of 50,000 cps. Subsequently, the mixture was poured into glass petri dishes and allowed to evaporate under air flow. Once in a solid state, 5 ml of polylactic acid solution was applied to form a capping layer. After evaporation, the sheet was removed from the petri dish, rotated 180 degrees, placed back in the petri dish and an additional 5 ml of polylactic acid solution was applied to form a second caping layer of the reverse side. The result was a sheet of solid polylactic acid containing spherical regions of modified boswellic acid.

Example D2: An Implant of the Present Invention with Porosity

A 20% solution of polylactic acid 704 (Boehinger-Ingelheim, Ridgefield, CT) and acetone was prepared. Into 50 ml of the polylactic acid solution was mixed 0.1 grams granulated oxidized cellulose. The mixture was mixed in a beaker under gentle agitation until the mixture reached a viscosity of 50,000 cps. Subsequently, the mixture was poured into glass petri dishes and allowed to evaporate under air flow. Thereto was poured 1 ml of modified boswellic acid. The modified boswellic acid was readily taken up by the oxidized cellulose, and the modified boswellic acid was spread across the formed sheet until a uniform absorption was obtained. The excess modified boswellic acid was removed with a light wash of isopropyl alcohol.

Example D3: An Implant of the Present Invention Utilizing a Polyurethane Copolymer The absorbable polyurethane prepolymer was dissolved in 50 ml of acetone. Twenty milliliters of this solution was poured into a glass petri dish and allowed to polymerize at ambient conditions for 24 hours. The result was a solid, non-porous sheet of polyurethane. To this was poured 1 ml of modified boswellic acid of Example 5, and the combination was allowed to stand until all the modified boswellic acid was absorbed into the polyurethane. The result was an absorbable polyurethane carrier with modified boswellic acid dissolved into the bulk volume of the polyurethane.

Example D4: A Porous Implant Utilizing a Polyurethane Copolymer

The absorbable polyurethane prepolymer (50 ml) was mixed under high shear with 1 ml modified boswellic acid. The resulting homogenous mixture was than mixed under high shear with 10 ml of water and rapidly poured into a glass petri dish. The result was an elastic foam, wherein the porosity was contained trapped modified boswellic acid.

What is claimed is:

1. A method for enhancing the therapeutic activity of a pentacyclic acidic fraction from *Boswellia* genus, said method comprising: attachment of a polyol to a hydroxyl group residing on a boswellic acid fraction derived from *Boswellia* extract via an isocyanate group to provide a product having enhanced biological activity, wherein an amount of *Boswellia* extract is used so that a percent nitrogen-carbon-oxygen (% NCO) content is equal to zero.

2. The method according to claim 1, wherein said polyol is comprised of one or more of polyethylene oxide and polypropylene oxide.

3. The method according to claim 1, wherein said polyol is attached to said boswellic acid fraction via one or more urethane links.

4. The method according to claim 1, wherein said product contains multiple boswellic acid fractions per molecule.

5. The method according to claim 1, wherein said polyol is an ethylene oxide.

6. The method according to claim 1, wherein said polyol is a propylene oxide.

7. The method according to claim 1, wherein said polyol is a copolymer of ethylene oxide and propylene oxide blocks.

8. The method according to claim 1, wherein said polyol contains greater than 2 hydroxyl groups.

9. The method according to claim 1, wherein the product comprises acetyl-11-keto-beta-boswellic acid (AKBA) in an amount greater than about 20% of the total boswellic acids by weight.

10. The method according to claim 1, wherein the method further comprises using a solubilizing agent and a physiologically compatible carrier.

11. The method according to claim 10, wherein said solubilizing agent is propylene carbonate.

12. The method according to claim 10, wherein said physiologically compatible carrier is propylene carbonate.

13. The method according to claim 10, wherein said solubilizing and carrier agents do not contain available hydroxyl groups.

* * * * *